US012429483B2

(12) United States Patent
Lapidot et al.

(10) Patent No.: US 12,429,483 B2
(45) Date of Patent: Sep. 30, 2025

(54) SYSTEM AND METHOD FOR DETERMINING ONSET AND DISEASE PROGRESSION

(71) Applicant: RESPIRATION SCAN LTD, Ness Ziona (IL)

(72) Inventors: Yaron Lapidot, Givat Ada (IL); Igal Moshe Bar Ilan, Hevel Korazim (IL)

(73) Assignee: RESPIRATION SCAN LTD, Ness Ziona (IL)

( * ) Notice: Subject to any disclaimer, the term of this patent is extended or adjusted under 35 U.S.C. 154(b) by 0 days.

(21) Appl. No.: 17/634,422

(22) PCT Filed: Aug. 13, 2020

(86) PCT No.: PCT/IL2020/050896
§ 371 (c)(1),
(2) Date: Feb. 10, 2022

(87) PCT Pub. No.: WO2021/028928
PCT Pub. Date: Feb. 18, 2021

(65) Prior Publication Data
US 2022/0317122 A1    Oct. 6, 2022

Related U.S. Application Data

(60) Provisional application No. 62/955,790, filed on Dec. 31, 2019, provisional application No. 62/885,847, filed on Aug. 13, 2019.

(51) Int. Cl.
*G01N 33/569* (2006.01)
*A61B 5/08* (2006.01)
*A61B 5/097* (2006.01)

(52) U.S. Cl.
CPC ........ *G01N 33/56911* (2013.01); *A61B 5/082* (2013.01); *A61B 5/097* (2013.01); *G01N 33/56983* (2013.01); *G01N 2333/195* (2013.01); *G01N 2333/21* (2013.01); *G01N 2800/26* (2013.01); *G01N 2800/50* (2013.01)

(58) Field of Classification Search
None
See application file for complete search history.

(56) References Cited

U.S. PATENT DOCUMENTS

| | | | |
|---|---|---|---|
| 9,733,225 B2 | 8/2017 | Armstrong | |
| 10,261,071 B2 | 4/2019 | Hall et al. | |
| 10,589,277 B2 * | 3/2020 | Ahmad | A61B 5/097 |
| 2002/0017125 A1 | 2/2002 | Lewis et al. | |
| 2005/0065446 A1 | 3/2005 | Talton | |
| 2008/0008666 A1 | 1/2008 | Phillips | |
| 2008/0009761 A1 | 1/2008 | Acker et al. | |
| 2012/0183949 A1 | 7/2012 | Hyde et al. | |
| 2012/0326092 A1 | 12/2012 | Haick et al. | |
| 2013/0261487 A1 | 10/2013 | Baker et al. | |
| 2014/0065602 A1 | 3/2014 | Milton et al. | |
| 2014/0336080 A1 | 11/2014 | Ruether et al. | |
| 2015/0064796 A1 | 3/2015 | Fu et al. | |
| 2017/0030892 A1 | 2/2017 | Fu et al. | |
| 2017/0045495 A1 | 2/2017 | Trowell et al. | |
| 2018/0246078 A1 | 8/2018 | Knobel et al. | |
| 2019/0274633 A1 | 9/2019 | Kuzelka | |

FOREIGN PATENT DOCUMENTS

| | | | | |
|---|---|---|---|---|
| CN | 104856679 A | | 8/2015 | |
| WO | WO 2005089310 | * | 9/2005 | |
| WO | WO-2005089310 A2 | * | 9/2005 | ............. A61B 5/097 |
| WO | WO-2012059763 A1 | * | 5/2012 | ............. A61B 5/082 |
| WO | 2015187938 A1 | | 12/2015 | |
| WO | 2018162513 A1 | | 9/2018 | |
| WO | 2019173501 A1 | | 9/2019 | |

OTHER PUBLICATIONS

Bos LD, Sterk PJ, Schultz MJ. Volatile metabolites of pathogens: a systematic review. PLoS Pathog. May 2013;9(5):e1003311. doi: 10.1371/journal.ppat.1003311. Epub May 9, 2013. PMID: 23675295; PMCID: PMC3649982. (Year: 2013).*

He S, Chen B, Li W, Yan J, Chen L, Wang X, Xiao Y. Ventilator-associated pneumonia after cardiac surgery: a meta-analysis and systematic review. J Thorac Cardiovasc Surg. Dec. 2014;148(6):3148-55.e1-5. (Year: 2014).*

Schnabel, R., Fijten, R., Smolinska, A. et al. Analysis of volatile organic compounds in exhaled breath to diagnose ventilator-associated pneumonia. Sci Rep 5, 17179 (2015). (Year: 2015).*

Lu CJ, Zellers ET. Multi-adsorbent preconcentration/focusing module for portable-GC/microsensor-array analysis of complex vapor mixtures. Analyst. Aug. 2002;127(8):1061-8. (Year: 2002).*

Filipiak et al. Breath analysis for in vivo detection of pathogens related to ventilator-associated pneumonia in intensive care patients: a prospective pilot study. J Breath Res. Jan. 5, 2015;9(1):0160 (Year: 2015).*

Cho, et al., "Two-Step Preconcentration for Analysis of Exhaled Gas of Human Breath with Electronic Nose", Sensors and Actuators B vol. 117, Issue 1, Dec. 15, 2005, pp. 50-57.

Schnabel, et al., "Electronic Nose Analysis of Exhaled Breath to Diagnose Ventilator-Associated Pneumonia", Respiratory Medicine, vol. 109, No. 11. http://dx.doi.org/10.1016/j.rmed.2015.09.014, Sep. 14, 2015, pp. 1-6.

Van Oort, et al., "BreathDx—Molecular Analysis of Exhaled Breath as a Diagnostic Test for Ventilator-Associated Pneumonia: Protocol for a European Multicentre Observational Study", BMC Pulmonary Medicine vol. 17, No. 1. DOI 10.1186/s12890-016-0353-7, 2017, pp. 1-8.

Van Oort, et al., "Exhaled Breath Metabolomics for the Diagnosis of Pneumonia in Intubated and Mechanically-Ventilated Intensive Care Unit (ICU)-Pateients", International Journal of Molecular Sciences. vol. 18, No. 22, 449. doi:10.3390/ijms 18020449, Feb. 19, 2017, pp. 1-14.

(Continued)

*Primary Examiner* — Janet L Andres
(74) *Attorney, Agent, or Firm* — Ballard Spahr LLP

(57) ABSTRACT

The invention disclosed herein concerns screening and early detection of a variety of disease conditions in seemingly healthy subjects, enabling early intervention and treatment.

22 Claims, 19 Drawing Sheets

(56) References Cited

OTHER PUBLICATIONS

Amann, "Breath Analysis for Clinical Diagnosis and Therapeutic Monitoring", Siriraj Med J, vol. 6, Suppl 2, Nov.-Dec. 2012, pp. 18-19.

Beale, et al., "A Review of Analytical Techniques and Their Application in Disease Diagnosis in Breathomics and Salivaomics Research", International Journal of Molecular Sciences, vol. 18, No. 24. doi:10.3390/ijms18010024, Dec. 23, 2016, pp. 1-26.

Bergmann, et al., "In Vivo Volatile Organic Compound Signatures of *Mycobacterium avium* Subsp. *paratuberculosis*", PLOS ONE, vol. 10, No. 4. https://doi. org/10.1371/journal.pone.0123980, Apr. 27, 2015, pp. 1-14.

Fowler, et al., "Surveillance For Lower Airway Pathogens in mechanically Ventilated Patients By Metabolomic Analysis of Exhaled Breath: A Case-Control Study", Thorax, vol. 70, No. 4. doi:10.1136/thoraxjnl-2014-206273, Feb. 6, 2015, pp. 1-6.

King, et al., "Measurement of Endogenous Acetone and Isoprene in Exhaled Breath During Sleep", IOP Publishing, Science Physiological Measurement vol. 33. doi: 10.1088/0967-3334/33/3/413, Feb. 28, 2012, pp. 413-428.

Lawal, et al., "Exhaled Breath Analysis: A Review of 'Breath-Taking' Methods For Off-Line Analysis", CrossMark, Metabolomics, vol. 13, No. 110. DOI 10.1007/s11306-017-1241-8, Aug. 19, 2017, pp. 1-16.

Lourenco, et al., "Breath Analysis in Disease Diagnosis: Methodological Considerations and Applicaitons", Metabolites, vol. 4. doi:10.3390/metabo4020465, Jun. 20, 2014, pp. 465-498.

Schnabel, et al., "Analysis of Volatile Organic Compounds in Exhaled Breath to Diagnose Ventilator-Associated Pneumonia", Scientific Reports, vol. 5, No. 1. DOI: 10.1038/srep17179, Nov. 26, 2015, pp. 1-10.

\* cited by examiner

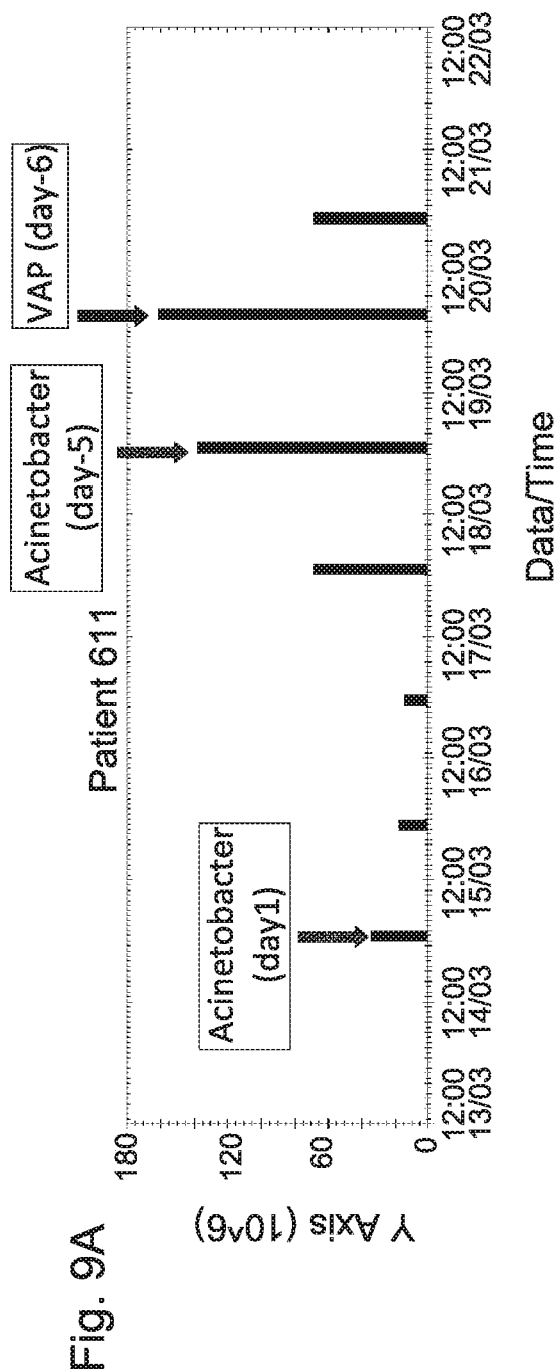
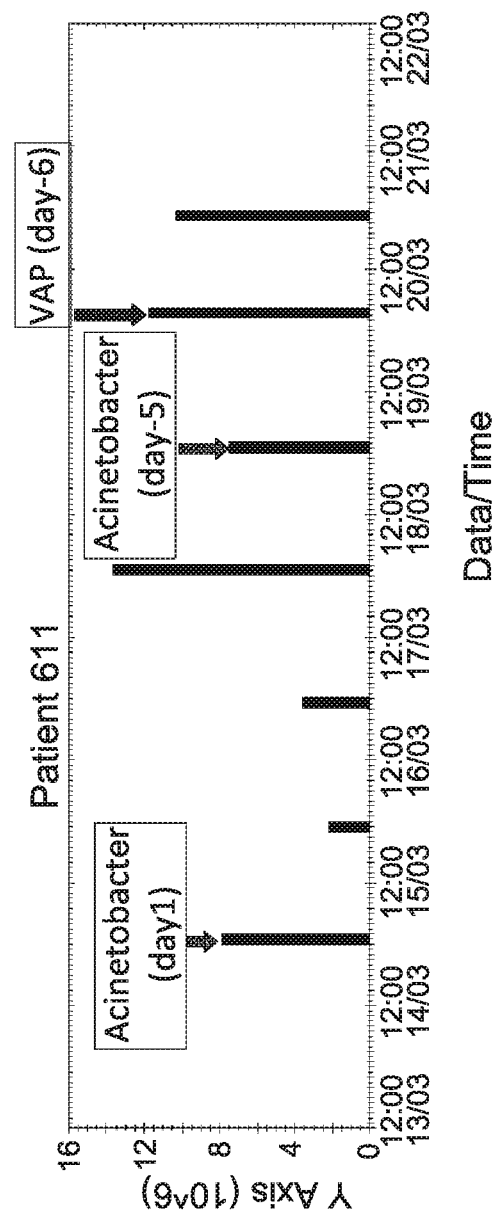

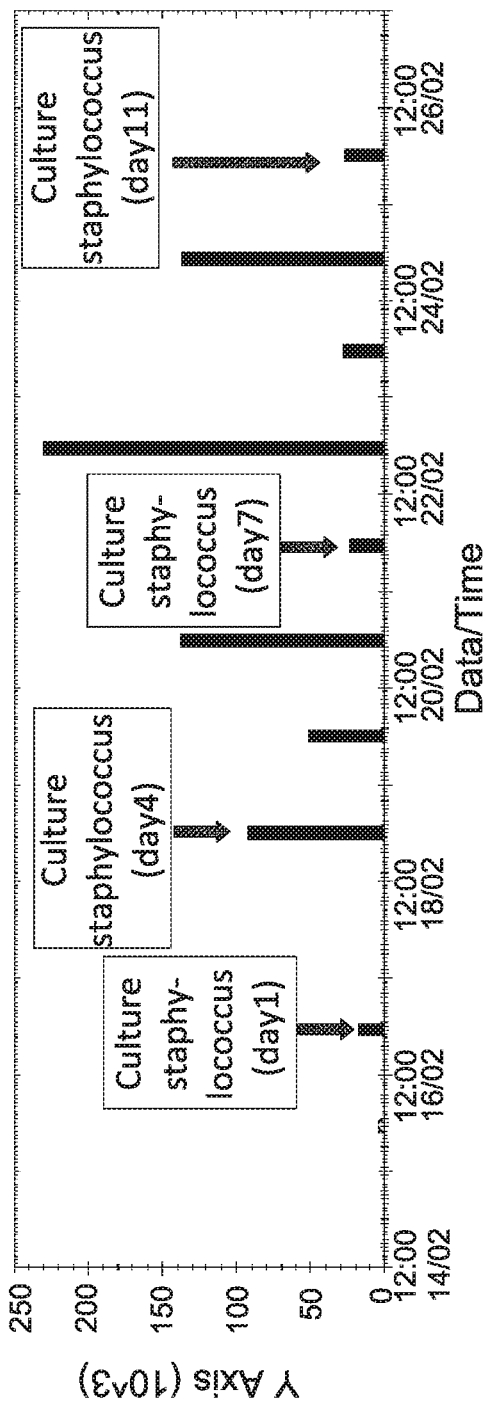
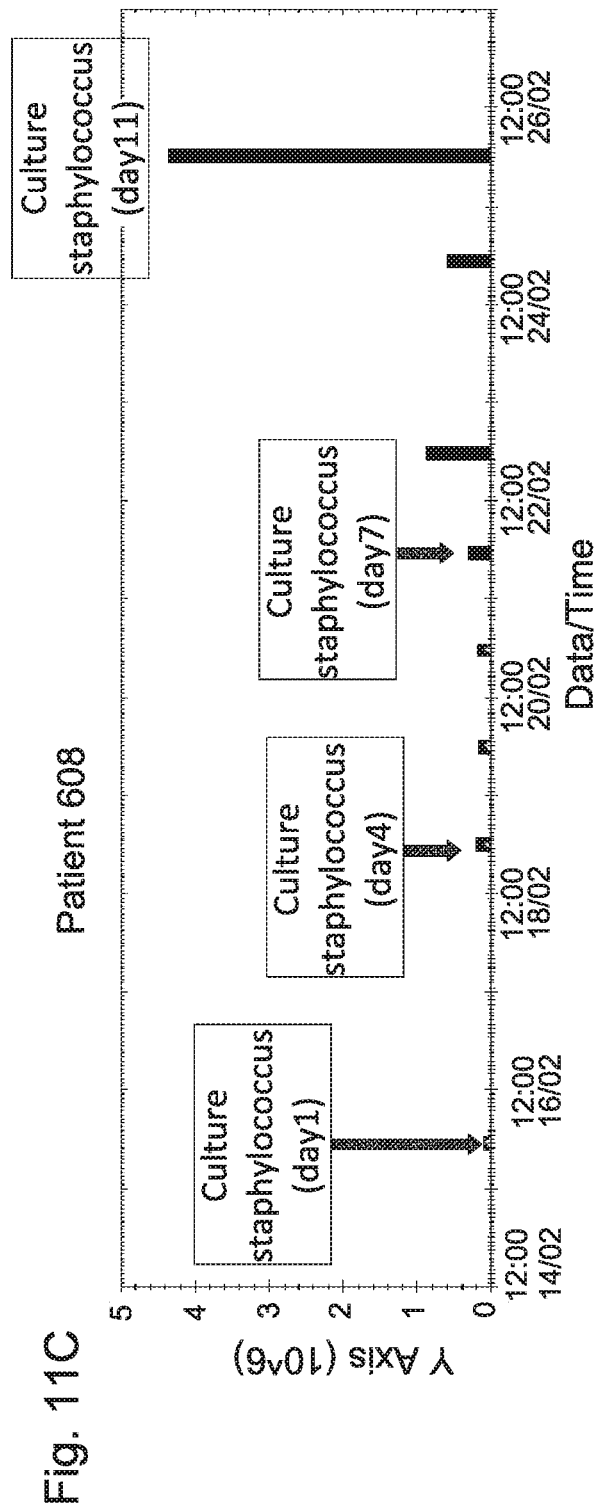
Fig. 11B
Fig. 11C

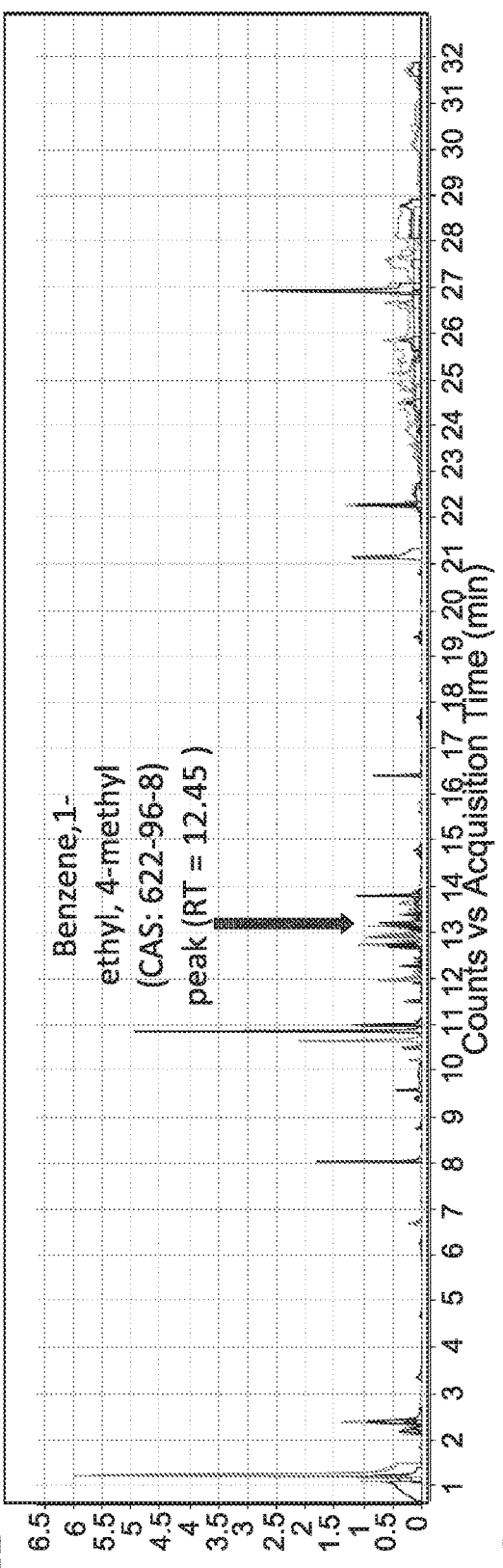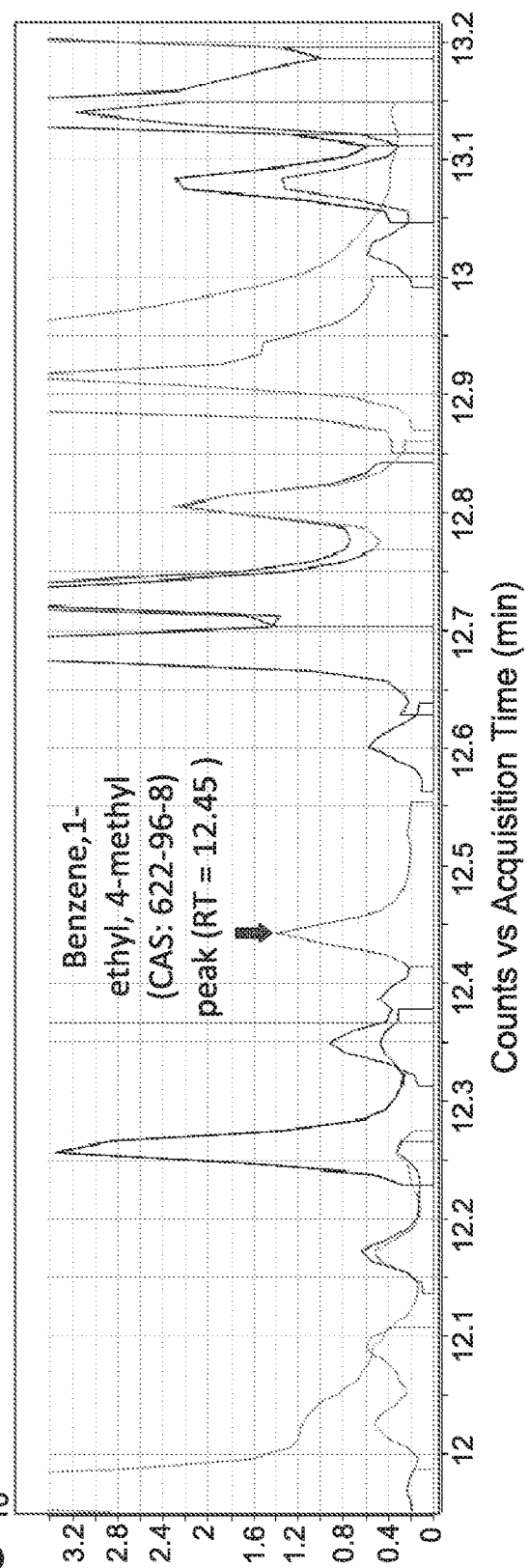

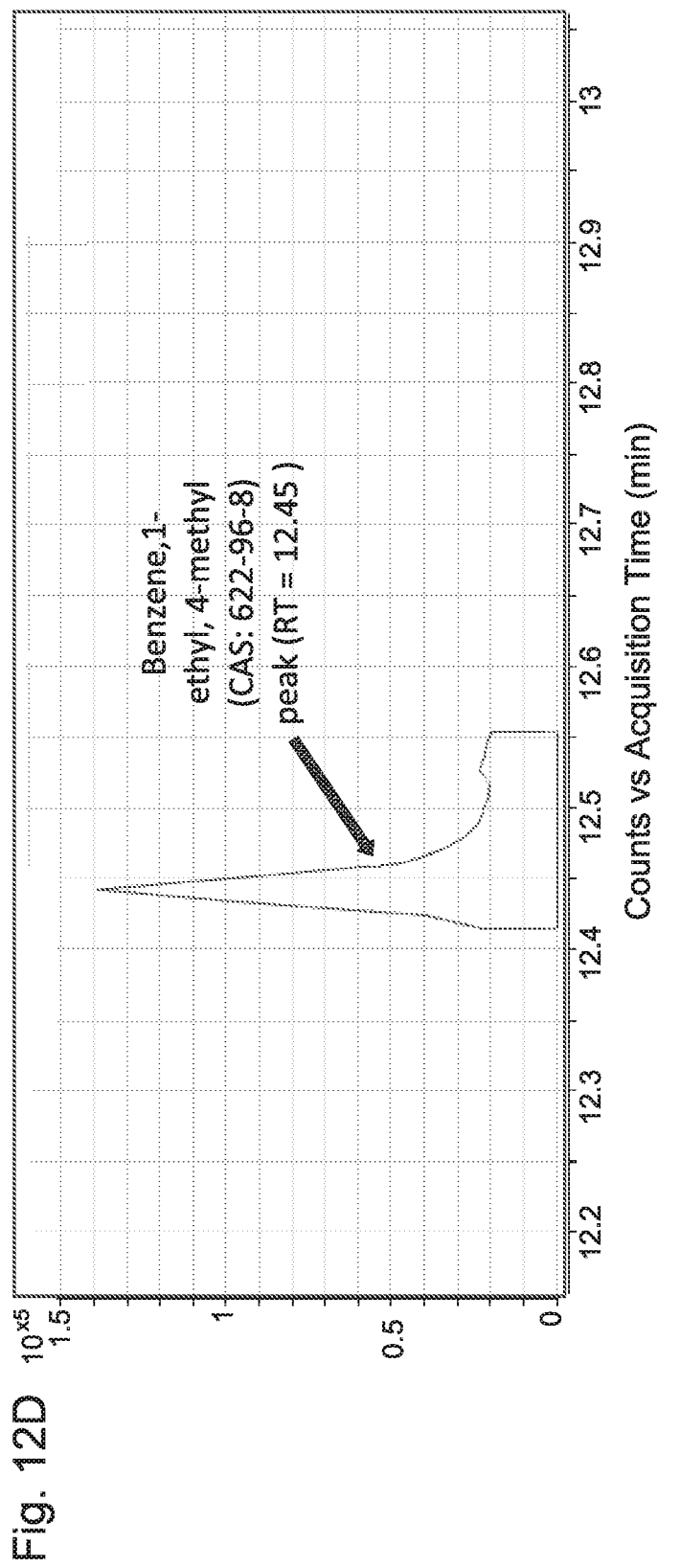

SYSTEM AND METHOD FOR DETERMINING ONSET AND DISEASE PROGRESSION

TECHNOLOGICAL FIELD

The present invention generally concerns a system and method for the determining onset and progression of disease states.

BACKGROUND

Air exhaled from the lungs carries volatile (and semi volatile) chemicals and metabolites that find their way to the lungs through the blood system. These chemicals and metabolites include agents which may be indicative of a person's health condition. Simple breath analyzers are configured and used for determining levels of alcohol or other volatile metabolites of drugs for forensic purposes, where the compounds of interest or their metabolites are well known. Breath analysis for identifying volatile compounds as indicators for clinical conditions is complex due to the large number of volatile compounds that are carried in the breath and their rather low concentrations.

Gas chromatography and EI mass spectra analysis were used for such analysis. International Patent Publication WO 2019/173501 [1] and US Patent Application No. 2019/0274633 [2] describe systems for determining the presence of volatile organic compounds in breath exhaled by a person being mechanically ventilated. These systems utilize the fact that the ventilator unit pressurizes inhaled air and hence both inlet and outlet lines can pressurize and therefore samples from the exhaled air can be collected on an adsorbent. The adsorbed compounds are analyzed by an analytical unit.

U.S. Pat. No. 9,733,225 [3] describes a replaceable spectroscopic detector used in volatile organic compounds testing devices, such as a portable breath testing device for roadside drug testing or a testing device for any air handling systems, which reversibly sorb compounds and prepare a concentrated sample in a single gas cell configured for performing spectroscopy of the contents within the cell.

US Patent Application No. 2008/0009761 [4] describes a breath condensate sampler for use with a mechanical ventilator, the breath condensate sampler comprises an airflow valve disposed in the expiratory limb of the ventilator, a condensate formation means, and a condensate collection means. The airflow valve directs air from the expiratory limb into the breath condensate sampler wherein the condensate portion of exhaled gases are separated from the gaseous portion of the exhaled gases. A method of collecting a breath condensate sample is also herein disclosed.

International Patent Publication WO 2015/187938 [5] describes methods for diagnosing, treating, and monitoring the treatment of invasive aspergillosis (IA). The methods can include detecting the presence of one or more volatile organic compounds (VOCs) in the breath of subjects suspected of having IA.

U.S. Pat. No. 10,261,071 [6] describes a set of volatile organic compounds, for breath analysis. The description includes methods of identifying these VOCs and use thereof in diagnosing, monitoring the onset of pulmonary toxicity are also disclosed.

BACKGROUND ART

[1] WO 2019/173501;
[2] US 2019/0274633;
[3] U.S. Pat. No. 9,733,225;
[4] US 2008/009761;
[5] WO 2015/187938;
[6] U.S. Pat. No. 10,261,071.

GENERAL DESCRIPTION

Early diagnosis of disease states in seemingly healthy or asymptomatic patients is typically reserved to patient populations that are either predisposed to attracting or suffering from a particular type of a disease or to patients with life threatening recurring conditions. Even where methodologies exist for achieving such early diagnosis, such diagnosis may involve, in addition to the routine laboratory tests, also the use of rather expensive diagnostic systems, and at times invasive diagnosis, which make early diagnosis in healthy patients less acceptable.

The inventors of the invention disclosed herein have developed a methodology that enables extensive screening and early detection of a variety of disease conditions in seemingly healthy subjects, enabling early intervention and treatment. Methods of the invention are non-invasive, do not require complex medical devices or hospitalization, are of low cost and provide an efficient means to diagnose and perform treatment monitoring by physicians or any other medical staff at any point of care, such as at the physician clinic or office, in emergency care units, clinical labs or pharmacies or at the subject's home.

The invention disclosed herein provides a method and a system for diagnosing, predicting or identifying an early onset of a disease in an asymptomatic subject or, more broadly, in the general population. The method involves detecting the presence of volatile organic compounds (VOCs) or semi-VOCs (sVOCs) (herein referred to as volatile compounds, VCs, or markers, in general) in exhaled breath samples. As the inventors have demonstrated, breath samples collected from subjects in the general population have been found to contain markers which presence and amount provide an indication to an existing disease state that has not manifested itself at the time of diagnosis. The ability to detect and monitor changes in the amount of the markers over time also provides the means to evaluate or monitor the evolution of a disease state over a period of time and asses relevance and success of a medical treatment.

Each disease state may be characterized by a different cluster of markers or marker-fingerprints that is unique and indicative of the specific disease state and can be used to differentiate the originator of one disease state over the other. For example, a marker-fingerprint characteristic of a bacterial infection may be different from a marker-fingerprint characteristic of a liver disease. Likewise, as marker-fingerprint characteristic of a specific bacterial infection may be different and distinct from a marker-fingerprint characteristic of another bacterial infection, differentiation between the two may be achieved.

More uniquely, the methodology of the invention permits identification of a disease state in subjects exhibiting symptoms associated with a different disease, wherein the methodology of the invention can differentiate between the two diseases. This unique ability appears mostly exceptional in a continuous diagnosis of evolving disease states in hospitalized patients, e.g., ventilated patients, who exhibit a plurality of medical complexities, and who are highly susceptible to contracting a nosocomial infection, i.e., a hospital-acquired infection (HAI). Early detection of such an infection can dramatically decrease the effect of life-risking complexities which can develop.

Thus, in a first of its aspects, the invention provides a method for determining presence of at least one disease-associated marker in a breath sample from a subject, the method comprising exposing to a breath sample of a subject at least one sampling unit comprising one or more adsorbing regions capable of reversibly associating volatiles in said breath sample;

analyzing the at least one sampling unit to identify volatiles adsorbed onto the one or more adsorbing regions and determining presence of said at least one disease-associated marker, wherein the presence of said marker at a level higher than a background level of said marker is indicative of existence of the disease state.

The "marker" is typically a volatile compound (VC) or a semi-volatile compound (VC), which may be an inorganic material or an organic material. Where the compound is an organic compound, it is referred to as a volatile organic compound (VOC) or a semi-volatile organic compound (sVOC). Within the context of the present invention, these terms are interchangeable.

The markers may be endogenous markers which originate from within the body of the subject reflecting its metabolism or exogenous markers which originate from external sources such as diet, prescription drugs and environmental exposures. As production of endogenous markers is linked directly to metabolic activity in the body, wherein clusters or combinations of such markers are characteristic of a specific disease process, presence and quantity (level, amount, concentration) of such endogenous markers in the breath of a subject and their development over time, provides a direct indication of a disease state. These markers are thus referred to herein as "disease-associated markers".

In most general terms, the markers are typically associated with metabolism, organ function, or presence and/or growth of a pathogen (e.g. bacteria, virus or fungus) that is involved in the pathogenesis of a disease. The markers that are generated in the body, e.g., through the metabolism of cells or pathogens within the body, are released into the circulatory system and thereafter excreted through the exhaled breath. The markers may comprise a plurality of compounds, some of which gaseous, others may be liquids (at a physiological temperature), which are released into the exhaled breath and carried by the breath gases or small droplets of water, and thus can be detected and quantified.

To distinguish between microorganisms (bacteria, viruses and fungi) that are present in a subject at low levels and are part of the subject microbiome from microorganisms which presence and load/amount/mass in indicative of pathogenesis, a method of the invention allows for both qualitative (i.e., determination of presence of the microorganism, e.g., pathogen) and quantitative (i.e., determination of the load/amount/mass of said microorganism) determination of pathogenesis. Thus, markers associated with microorganisms typically present in a subject microbiome will be regarded indicative of a pathogenic pathway when their measured amount is at least doubled within two days from the initial measurement. The initial measurement being the background level measured in a healthy person or in the person that is monitored. Thus, a marker or a cluster of markers are indicative when an increase in their amount of at least 50% each day (overall more than doubled) is observed between two consecutive measurements.

As used herein, the marker may be a single molecule or a combination of several molecules, wherein methods of the invention are similarly applicable for diagnosis based on a single marker, a combination of markers or a marker fingerprint. Thus, the singular form of the term encompasses also a plurality of markers.

The "marker fingerprint" refers to a collection of properties relating to the marker content of the exhaled breath obtained from a subject. These collective properties are unique and informative, may be regarded as a fingerprint or a signature indicating onset, evolution or progression of a certain disease over the other. The profile differentiating one disease over the other can also provide an insight as to the state of the disease or the progression thereof, can identify the onset of the disease at an early stage before symptoms develop and can assist in determining success of a therapeutic treatment (prophylaxis or treatment of existing symptoms). The properties may be one or more of:

presence or absence of one or more marker indicative of a disease,
the concentration (or amount) of the one or more marker,
evolution (an increase or decrease in concentration or amount) over time, particularly in cases of exponential growth,
the presence or absence of other markers in combination,
the ratio amounts between the various markers, and
a change in the presence or amount of one or more markers over time.

The marker may be any marker known to be associated with a disease condition. Some of these markers may be selected from 1,8-naphthyridine, 10-undecyn-1-ol, 3-methyl-1-butanol, 1-phenyl-1H-imidazole, 2-(2-pyridinyl)-1H-indole, 8-methyl-1H-purine, 1-methoxyphthalazine, 1-nitro-2-propanol, 2-butyl-1-octanol, 3,7-dimethyl-1-octanol, 2-methyl-1-propanol, 1-undecene, 2-(2-methylpropyl)-3,5-di(1-methylethyl)pyridine, 2,3-dimethylcyclohexylamine, 2,4-dithiapentane, 2-benzyl-1-methylpiperidine, 2-butanone, 3-propylidene-2-heptanone, 6-phenylhexanoic acid, 8-aminocaprylic acid, 2,2'-thiobis-acetic acid, acetone, O-isopropyloxime benzaldehyde, 4-nitro-benzamide, 2-carboxy-benzeneacetic acid, 2-methyl-butanal, 3-methyl-butanal, 3-methyl-butanoic acid, dodecamethyl-cyclohexasiloxane, cyclohexene, D:C-Friedours-7-ene, dimethyl trisulfide, dimethyl disulfide, emorfazone (4-ethoxy-2-methyl-5-morpholin-4-ylpyridazin-3-one), ethylphenylhydantoin, gabapentin lactam, ethyl 5-oxohexanoate, 5-nitro-isoquinoline, lanostan-12-one, luminol (5-amino-2,3-dihydrophthalazine-1,4-dione), 4-butyl-phenol, phthalic anhydride, pregabalin, 1-(ethynylsulfinyl)-propane, ribo-ribo disaccharide, S-(2-benzothiazolyl)cysteine, 2-butyl-5-ethyl-thiophene, cyclopropyl carbinol, 2-pyridinecarbonitrile, 2-bromo-1-(4-methylphenyl)-ethenone, 2,3,4,7-tetrahydro-1H-indene, 1-bromo-1-phenylpropane, 2,6-dimethyldecane, N,N-dimethyl-1-dodecanamine, 3-methyl-6-(1-methylethylidene)-cyclohexene, 8-methyl-1-decene, 6-methyl-dodecane, N,N-dimethyl-1-tetradecanamine, hexanedioic acid bis(2-ethylhexyl) ester, (+)-4-carene, 2-carene, 2-methyl-1-propene, 4,11,11-trimethyl-8-methylene-bicyclo[7.2.0]undec-4-ene, 3-methylpentan-2-yl trifluoroacetate, 2-methyl-5-(1-methylethenyl)-cyclohexanol, (Z)-4-Decen-1-ol trifluoroacetate, 4-methyl-1-(1-methylethyl)-bicyclo[3.1.0]hexan-3-ol, pyruvic acid butyl ester, 2,9-dimethyl-decane, propylamine, ethylenediamine, 1-methyl-2-(3-methylpentyl)-cyclopropane, (nitromethyl) benzene, 5-ethyl-1-nonene, isopropylsulfonyl chloride, deltacyclene, 2,3,6,7-tetramethyl-octane, 1-methyl-4-(1-methylethenyl)-benzene, 3,4-dimethyl-1-pentene, N-benzyl-N-methyl-2-methyl-β-alanine methyl ester, 2,2,4-trimethyl-pentane, trans-geranylgeraniol, 2-ethyl-4-methyl-1-pentanol, 6-methylheptyl vinyl ether, tetrahydro-6-methyl-2H-pyran-2-one, 2,3,7-trimethyl-decane, 2-decen-1-ol, (1R,4aS,8aR)-1-isopropyl-4,7-dimethyl-1,2,4a, 5,6,8a-hexahydronaphthalene, 3-ethyl-2-methyl-hexane, 2-methyl-1-pentene, 4,5-dimethyl-undecane, 4-methylene-1-methyl-2-(2-methyl-1-propen-1-yl)-1-vinyl-cycloheptane, 7-methyl-(E)-4-decene, 1-iodo-dotriacontane, 5-dodecyldihydro-2(3H)-furanone, butyl dodecyl ester sulfurous acid, 3 4-dimethylbenzyl alcohol, 1,4-dimethyl-cyclooctane, 2,3-dimethyl-hexane, dodecanoic acid, estragole, 4-ethyl-1-octyn-3-ol, 5-methyl-2-(1-methylethyl)-1-hexanol, 3,3-dimethyl-heptane, 7-methyl-(Z)-2-decene, 2-methyl-decane, 1,2,3,4,4a,5,6,7,8,9,10,10a-dodecahydro-1,4a-dimethyl-7-(1-methylethyl)-1-phenanthrenecarboxylic acid methyl ester, dodecanal, 1-octadecanesulphonyl chloride, 4-tert-butylcyclohexyl acetate, 4-hexen-2-one, 2,5,6-trimethyl-decane, 4 4-dimethyl-1-hexene, heptadecane, isobutylene epoxide, 2,2,7,7-tetramethyloctane, 2-ethyl-1-hexanol trifluoroacetate, propylcyclopropane, anethole, octane, methyl-cyclobutane, 1,12-dodecanediol, 2-methoxy-1-propene, nitrous acid, 4-(1,1-dimethylethyl)cyclohexanol acetate, 1,5-dimethyl-8-(1-methylethylidene)-(E E)-5-cyclodecadiene, 4-methyl-2-propyl-1-pentanol, octahydro-4-methyl-8-methylene-7-(1-methylethyl)-[1S-(1α,3αβ,4α,7α, 7αβ)]-1,4-methano-1H-indene, 3-ethyl-2,7-dimethyl-octane, hexyl pentyl ether, 1,2-diphenyl-(R*,R*)-1,2-ethanediol, 7-ethyl-1,2,3,4,4a,5,6,7,8,9,10,10a-dodecahydro-1,4a,7-trimethyl-methyl ester [1 S-(1α,4aα,7β,10αβ)]-1-phenanthrenecarboxylic acid.

In some embodiments, markers associated with at least one bacterial pathogen are selected from 1,8-naphthyridine, 10-undecyn-1-ol, 3-methyl-1-butanol, 1-phenyl-1H-imidazole, 2-(2-pyridinyl)-1H-indole, 8-methyl-1H-purine, 1-methoxyphthalazine, 1-nitro-2-propanol, 2-butyl-1-octanol, 3,7-dimethyl-1-octanol, 2-methyl-1-propanol, 1-undecene, 2-(2-methylpropyl)-3,5-di(1-methylethyl)pyridine, 2,3-dimethylcyclohexylamine, 2,4-dithiapentane, 2-benzyl-1-methylpiperidine, 2-butanone, 3-propylidene-2-heptanone, 6-phenylhexanoic acid, 8-aminocaprylic acid, 2,2'-thiobis-acetic acid, acetone, 0-isopropyloxime benzaldehyde, 4-nitro-benzamide, 2-carboxy-benzeneacetic acid, 2-methyl-butanal, 3-methyl-butanal, 3-methyl-butanoic acid, dodecamethyl-cyclohexasiloxane, cyclohexene, D:C-Friedours-7-ene, dimethyl trisulfide, dimethyl disulfide, emorfazone (4-ethoxy-2-methyl-5-morpholin-4-ylpyridazin-3-one), ethylphenylhydantoin, gabapentin lactam, ethyl 5-oxohexanoate, 5-nitro-isoquinoline, lanostan-12-one, luminol (5-amino-2,3-dihydrophthalazine-1,4-dione), 4-butyl-phenol, phthalic anhydride, pregabalin, 1-(ethynylsulfinyl)-propane, ribo-ribo disaccharide, S-(2-benzothiazolyl)cysteine and 2-butyl-5-ethyl-thiophene.

In some embodiments, markers associated with viral pathogens are selected from cyclopropyl carbinol, 2-pyridinecarbonitrile, 2-bromo-1-(4-methylphenyl)-ethenone, 2,3,4,7-tetrahydro-1H-indene, 1-bromo-1-phenylpropane, 2,6-dimethyldecane, N,N-dimethyl-1-dodecanamine, 3-methyl-6-(1-methylethylidene)-cyclohexene, 8-methyl-1-decene, 6-methyl-dodecane, N,N-dimethyl-1-tetradecanamine, hexanedioic acid bis(2-ethylhexyl) ester, (+)-4-carene, 2-carene, 4,11,11-trimethyl-8-methylene-bicyclo[7.2.0]undec-4-ene, 3-methylpentan-2-yl trifluoroacetate, 2-methyl-5-(1-methylethenyl)-cyclohexanol, (Z)-4-Decen-1-ol trifluoroacetate, 4-methyl-1-(1-methylethyl)-bicyclo[3.1.0]hexan-3-ol, pyruvic acid butyl ester, 2,9-dimethyl-decane, propylamine, ethylenediamine, 1-methyl-2-(3-methylpentyl)-cyclopropane, (nitromethyl)benzene, 5-ethyl-1-nonene, isopropylsulfonyl chloride, deltacyclene, 2,3,6,7-tetramethyl-octane, 1-methyl-4-(1-methylethenyl)-benzene, 3,4-dimethyl-1-pentene, N-benzyl-N-methyl-2-methyl-β-alanine methyl ester, 2,2,4-trimethyl-pentane, trans-geranylgeraniol, 2-ethyl-4-methyl-1-pentanol, 6-methylheptyl vinyl ether, tetrahydro-6-methyl-2H-pyran-2-one, 2,3,7-trimethyl-decane, 2-decen-1-ol, (1R,4aS,8aR)-1-isopropyl-4,7-dimethyl-1,2,4a,5,6,8a-hexahydronaphthalene, 3-ethyl-2-methyl-hexane, 2-methyl-1-pentene, 4,5-dimethyl-undecane, 4-methylene-1-methyl-2-(2-methyl-1-propen-1-yl)-1-vinyl-cycloheptane, 7-methyl-(E)-4-decene, 1-iodo-dotriacontane, 5-dodecyldihydro-2(3H)-furanone, butyl dodecyl ester sulfurous acid, 3 4-dimethylbenzyl alcohol, 1,4-dimethyl-cyclooctane, 2,3-dimethyl-hexane, dodecanoic acid, estragole, 4-ethyl-1-octyn-3-ol, 5-methyl-2-(1-methylethyl)-1-hexanol, 3,3-dimethyl-heptane, 7-methyl-(Z)-2-decene, 2-methyl-decane, 1,2,3,4,4a,5,6,7,8,9,10,10a-dodecahydro-1,4a-dimethyl-7-(1-methylethyl)-1-phenanthrenecarboxylic acid methyl ester, dodecanal, 1-octadecanesulphonyl chloride, 4-tert-butylcyclohexyl acetate, 4-hexen-2-one, 2,5,6-trimethyl-decane, 4 4-dimethyl-1-hexene, heptadecane, isobutylene epoxide, 2,2,7,7-tetramethyloctane, 2-ethyl-1-hexanol trifluoroacetate, propylcyclopropane, anethole, octane, methylcyclobutane, 1,12-dodecanediol, 2-methoxy-1-propene, nitrous acid, 4-(1,1-dimethylethyl)cyclohexanol acetate, 1,5-dimethyl-8-(1-methylethylidene)-(E E)-5-cyclodecadiene, 4-methyl-2-propyl-1-pentanol, octahydro-4-methyl-8-methylene-7-(1-methylethyl)-[1S-(1α,3αβ,4α,7α, 7αβ)]-1,4-methano-1H-indene, 3-ethyl-2,7-dimethyl-octane, hexyl pentyl ether, 1,2-diphenyl-(R*,R*)-1,2-ethanediol and 7-ethyl-1,2,3,4,4a,5,6,7,8,9,10,10a-dodecahydro-1,4a,7-trimethyl-methyl ester [1 S-(1σ,4aα,7β, 10αβ)]-1-phenanthrenecarboxylic acid.

The "breath sample" is a sample obtained actively or passively from the subject's exhaled breath. Passive sampling involves capturing of the volatiles without applying any specific intervention. An example of passive sampling is a sampling unit that is equipped with an opening designed for Venturi effect. Active sampling involves capturing the volatiles through the implementation of, e.g., a pump (mechanical, electric, Helium or other) or a suction unit. Depending on the type of disease to be detected, e.g., whether a disease of an internal organ or a disease of the GI track, the breath sample may be an alveolar breath sample or a non-alveolar breath sample. Typically, samples are collected directly into the sampling units and the volatiles are allowed to interact by adsorption to the one or more adsorbing regions. Where the subject's full cooperation is provided, the subject exhales into the sampling units and the samples are thereafter processed. Where cooperation of the subject is not possible, samples may be collected from the subject's oral cavity or from the lungs. Samples from subjects on ventilation machines may be obtained by associating the sampling units to the outlet line of the respiration unit, as disclosed herein.

In some embodiments, the method comprises obtaining a breath sample from a subject by employing any non-invasive means known in the art. Non-limiting methods for collecting exhaled breath samples may involve the use of apparatuses approved by the American Thoracic Society/European Respiratory Society (ATS/ERS), see for example Silkoff et al., Am. J. Respir. Crit. Care Med., 2005, 171, 912.

In some embodiments, the sample may be obtained by direct exhalation of breath into a measuring device or apparatus.

The breath sample is collected by directly exhaling breath into the adsorbing/sampling unit(s). According to such embodiments, the breath sample may be captured using a mouthpiece that provides an interphase between the subject and the unit(s) operated according to methods of the invention. As the concentration of the markers in human breath may be in the range of ppm to ppt, the method may comprise a step of pre-concentrating the obtained sample of exhaled breath prior to analysis. Breath concentrators that are within the scope of the present invention include but are not limited to those described in US 2012/0326092 which is herein incorporated by reference.

The "sampling unit" is a container or a vessel or a canister of any shape or size configured for receiving and holding a breath sample. The sample unit may be a single unit or a plurality of such units. The sampling unit is typically made of a material that is substantially unreactive towards or exhibits a limited interaction with the volatiles, or markers contained in the breath sample. Thus, the unit is typically formed of materials such as glass or stainless steel. The sampling unit(s) comprises one or more (or a plurality of) adsorbing regions, each being capable of reversibly associating to volatiles in said breath sample. The adsorbing regions may be configured to fill the volume of the sampling units, or are formed on the inner surface of the sampling units walls, or present at any internal region of the sampling unit. The regions are nonetheless configured for selective binding of certain volatiles, in which case other volatiles are not adsorbed and can thus be removed or not detected; or may be configured for adsorbing any material present in the sample. Such a non-selective configuration may nevertheless prevent association of water and other background gases, such as oxygen and carbon dioxide, that may be present in the samples and which may complicate the collection, detection and measurement of the marker and marker concentration.

Distribution of adsorbing regions or the sorbent materials in each of the sampling units may vary in relative location and/or relative concertation and/or packing form. Solid sorbents are selected for sampling specific compounds in air due to their ability to (1) trap and retain the compound(s) of interest even in the presence of other compounds; (2) they do not chemically alter the compound(s) of interest; and (3) they allow the adsorbed compounds to be easily desorbed or extracted for analysis.

The adsorbing regions are structured of a material that is configured to physically trap the volatile materials. The materials may be characterized by presence of surface pores, surface roughness, increased surface area, and the like. Notwithstanding the structural characteristics, the adsorptive surface or material may be tailored for selective adsorption, as disclosed herein, or a non-selective adsorption.

In some embodiments, the adsorbing regions are formed of a material selected from organic porous polymers such as poly(2,6-diphenyl-p-phenylene oxide (PPPO), sulfonated polymers, ion-exchange resins, carbon molecular sieves that are prepared by controlled pyrolysis of poly(vinylidene chloride) or sulfonated polymers, and others.

In some embodiments, the adsorptive material is selected amongst carbon allotropes or carbonaceous materials, such as carbon nanotubes, graphene, fullerenes, carbon black, activated charcoal and others; cellulosic materials such as cellulose nanocrystals, cellulose fibers, nano fibrillated cellulose and others; silica gel; and others.

In some embodiments, the adsorbent is a carbon adsorbent such as CARBOTRAP® F, CARBOTRAP® C, CARBOTRAP® Y, CARBOTRAP® B, CARBOTRAP® X, CARBOPACK™ F, CARBOPACK™ C, CARBOPACK™ Y, CARBOPACK™ B, CARBOPACK™ X, CARBOXEN® 1016, CARBOXEN® 569, CARBOXEN® 1021, CARBOXEN® 1018, CARBOSIEVE™ S-III, CARBOXEN® 1003, CARBOSIEVE™ G, CARBOXEN® 1000 and CARBOXEN® 1012.

In some embodiments, carbon adsorbents may also be selected amongst graphitized carbon blacks having a 20/40 mesh, graphitized carbon blacks having a 60/80 mesh and carbon molecular sieves.

In some embodiments, the adsorbents having a surface area between 5 and 1500 $m^2/g$, a density of between 0.2 and 0.7 and/or a micropore diameter between 4 and 300 Å.

Alternatively, the adsorbing regions may be structured of a substrate material decorated with a plurality of binding molecules that can reversibly associate to the volatiles. These binding molecules are at least bifunctional (namely may have two or more functionalities) molecules having at least one functionality that associates the molecule to the surface and at least one other functionality that is capable of reversibly associating to the volatiles. The association may be any chemical association that is reversible, including ionic association, covalent association, H-bonding or complexation.

Excluded from the present invention is any adsorbing region that is metal based. This includes metal nanoparticles of any sort, metallic surfaces, metal matrices and others. In other words, the adsorbing regions are free or do not comprise or exclude any of the metallic forms above.

Exposure of the at least one sampling unit to a subject's breath may be achievable by placing the unit(s) in the path of the exhaled breath. This may be achieved, as disclosed herein, by having the subject breath directly into a unit, e.g., through a mouthpiece, or by associating the unit(s) to a ventilation unit to which the subject is connected, or by removing a sample from the subject's lungs. Notwithstanding the means, the exposure may be a single exposure, a plurality of exposures, a continuous exposure over a period of time, or timed exposures, wherein, e.g., the units are exposed at certain time points for a predetermined period. For the purpose of determining the presence of markers in the breath, the sampling units may be exposed at different sessions, namely at different time points and for different or same durations, and upon each exposure the unit may be analyzed, as disclosed herein, to determine the presence of the marker. The duration of each exposure session may be the same or different and may vary between several minutes to several hours or more. A first session identifying the presence of a marker may be regarded as the disease onset, as further discussed below.

The exposure session may also be structured (time and duration) to provide information as to a change (an increase or a decrease) in a marker concentration. An increase, e.g., which may be an exponential increase, in a marker concentration over time is typically indicative of an increase in the e.g., bacterial or vial amount or mass or load. Such an increase may be used to determine beginning of treatment, success of a medical treatment, modulation of treatment etc, as further disclosed herein.

Following exposure of the adsorbing regions to a breath sample, the various volatiles become adsorbed on the regions' surface or functionalities, as disclosed, and trapped/ associated until analyzed. To enable analysis of the adsorbed volatiles, the adsorbing regions are treated to cause desorption or dissociation of the volatiles from the surface, and the volatiles are thereafter analyzed. Desorption or dissociation of the volatiles from the adsorbing regions may be achieved thermally, under a flow of an inert gas, under vacuum or by employing any means that can release the volatiles into the analyzer. Thus, as used herein, the expression " . . . analyzing the at least one sampling unit to identify the volatiles adsorbed onto the one or more adsorbing regions to determine presence of . . . " refers to analyzing the volatiles which had been adsorbed and thereafter released from the adsorbing regions. The analysis need not identify each and every material or volatile in the sample but should provide the identification of the desired marker. Therefore, the analytical system or analyzer utilized may be any equipment or device that enables chemical or spectroscopic identification of the volatiles. The analysis may be achieved by any one or more of gas-chromatography (GC), GC-lined mass-spectrometry (GC-MS), proton transfer reaction mass-spectrometry (PTR-MS), electronic nose device (E-nose), quartz crystal microbalance (QCM), infra-red spectroscopy (IR), ultraviolet spectroscopy (UV) and others. The analysis may be configured to identify a single marker molecule or a cluster of molecules. In some cases, chemical identification of the marker may not be required; but rather a determination of a chemical profile (fingerprint), as defined herein.

In some embodiments, the analytical system utilized for the analysis of the desorbed volatiles is selected amongst GC, MS and GCMS. In some embodiments, the analytical system is selected from GCMS with TOF, Marke Bench-TOF-HD, Time-of-flight mass spectrometer for GC ALIGENT® 7890 and GC×GC modulator, including the option of collecting different collision energies at the same time, Quadrupole GCMS, ALIGENT® GC 6890 with ALIGENT® MSD 5975, ALIGENT® GC 7890B with ALIGENT® MSD 5977B, Quadrupole GCMS, ALIGENT® GC 7890 with ALIGENT® MSD 5975, Quadrupole GCMS, ALIGENT® GC 6890 with ALIGENT® MSD 5973, GCMS, ALIGENT® 7250 GC/Q-TOF, GCMS, ALIGENT® 7010B Triple Quadrupole GC/MS, GCMS, Thermo Scientific Q Exactive™ GC Orbitrap™ M GC-MS/MS and others.

In some embodiments, the analytical system is equipped with a first (main non-polar) column selected from SGEPN 99054140 (SN: 073438A23), 20M×0.18 mmID-BPX5×0.18 µm df, with He flow of 0.5 ml/min (Constant flow/pressure), and with a second column (being a polar column) selected from ALIGENT® DB5-ms 30M×0.25 mmID×0.50 µm df, with He flow of 1.5 ml/min (Constant flow/pressure).

Depending on the method used for analysis, in some embodiments, identification of markers is achieved by their retention time and relative retention time. As such, in some cases, disease-specific markers or pathogen-specific markers have a characteristic fingerprint of compounds or compound combinations that is released, and which presence and concentration is indicative of that specific disease or pathogen. Hence for example two different bacterium may release identical markers, however, in different concentrations. In some cases, therefore, only the full fingerprint, which includes marker identity and concentration serves as evidence for the presence of the disease or pathogen. In other cases, a single marker may be used.

The subject to be diagnosed according to methods of the invention is a human or a non-human subject. In most general terms, as disclosed herein, the subject may be a healthy subject, namely a subject not known to suffer from a chronic or an acute medical condition. The healthy subject may also be one suffering from a chronic health condition; however, at the time of diagnosis in accordance with methodologies disclosed herein, the subject exhibits no symptoms associated with the chronic disease. The subject may also be a diseased subject who at the time of diagnosis exhibits a state of an active disease, namely having symptoms associated with the disease.

In some embodiments, the subject is an asymptomatic subject.

In some embodiments, at the time of diagnosis the subject is suffering from a disease and the diagnosis aims at determining onset of a different disease state.

In some embodiments, the subject is a ventilated subject. In some embodiments, the method is aimed at detecting ventilator-associated pneumonia (VAP) in a subject connected to a respiratory system (a ventilated or intubated subject).

Ventilator-associated pneumonia is pneumonia that develops at least 48 hours after endotracheal intubation. This disease is distinct from hospital-acquired pneumonia, which is pneumonia that develops at least 48 hours after hospital admission in inpatients who are not receiving mechanical ventilation. Diagnosis of both conditions is imperfect. In practice, ventilator-associated pneumonia is often suspected based on the appearance of a new infiltrate on a chest x-ray that is taken for evaluation of new symptoms or signs such as fever, increased secretions, worsening hypoxemia or of leukocytosis that appear. As no symptom, sign, or x-ray finding is sensitive enough or specific for diagnosis, let alone early diagnosis, and as in the majority of cases diagnosis is initiated only upon appearance of symptoms, broad or pathogen-specific antibiotic treatment at a stage following development of symptoms does not always improve the subject's condition.

Methods of the invention offer the possibility of an early detection of the presence of a variety of pathogens in the subject's respiratory system at a stage prior to a stage when the pathogen spreads from a diseased organ, e.g., lung, to other organs and before symptoms appear. The pathogens may be hospital acquired or which are acquired through the air (airborne exposure), by direct or indirect contact, through sexual contact, or through contact with various body fluids such as blood, breast milk, semen and others.

The pathogens are typically selected amongst bacteria, viruses and fungi. In some embodiments, the pathogen is a bacterium. In some embodiments, the pathogen is a virus and in other embodiments, the pathogen is a fungus.

Methods of the invention are aimed at detecting the presence of a virus selected from any of the following virus families Coronaviridea, Adenoviruses, Arboviruses, Arenaviruses, Encephalitis, Orthomyxoviruses, Papillomaviruses, Paramyxoviruses, Picornaviruses, Poxviruses, Retroviruses, Rhabdovirus and Rhinoviruses.

In some embodiments, the virus is selected amongst coronaviruses, Variola major and other pox viruses; Arenaviruses such as Junin virus, Machupo virus, Guanarito virus, ymphocytic choriomeningitis virus, Lassa virus; Bunyaviruses such as Hantaviruses, Rift Valley fever virus; Flaviruses such as Dengue fever viruses; Filoviruses such as Ebola virus, Marburg virus; Eastern equine encephalitis virus, Western equine encephalitis virus, Venezuelan equine encephalitis virus, La Crosse virus, Japanese encephalitis virus, Kyasanur forest virus, California encephalitis viruses; food and waterborne pathogens such as Caliciviruses; Hepatitis A virus; Nipah virus; Yellow fever virus; Influenza viruses; Rabies virus and other Hantaviruses.

In some embodiments, the virus is an enveloped or non-enveloped virus. In some embodiments, the virus is a non-enveloped virus such as norovirus or parvovirus.

In some embodiments, the virus is an enveloped virus such as an influenza virus or a coronavirus such as SARS-CoV-2.

In some embodiments, the virus is a corona virus.

In some embodiments, the virus is SARS-CoV-2.

Where the pathogen is a bacterium, the bacterium may be selected from *Bacillus anthracis; Clostridium botulinum; Francisella tularensis; Yersinia pestis; Burkholderia pseudomallei; Burkholderia mallei; Clostridium perfringens; Coxiella burnetii; Brucella melitensis, abortus,* suis and *canis; Staphylococcus aureus; Rickettsia prowazekii; Chlamydia psittaci;* Food and Waterborne Pathogens such as *Escherichia coli, Vibrio cholerae, Salmonella* species, *Shigella* species, *Listeria monocytogenes, Campylobacter jejuni, Yersinia enterocolitica; Mycobacterium tuberculosis;* and other *Rickettsia*.

In some embodiments, the microorganism is one causing a so-called hospital associated infection (HAI), such as methicillin-resistant *Staphylococcus aureus* (MRSA). Other HAI caused microorganisms include vancomycin-resistant enterococci (VRE), *Clostridium difficile, Acinetobacter baumannii* and multi-drug resistant (MDR) *Acinetobacter* sp.

The fungi may be selected from *Candida, Aspergillus, Cryptococcus, Histoplasma, Pneumocystis* and *Stachybotrys*.

In some embodiments, the fungus is selected from *Candida albicans, Candida amphixiae, Candida antarctica, Candida argentea, Candida ascalaphidarum, Candida atlantica, Candida atmosphaerica, Candida auris, Candida blankie, Candida blattae, Candida bracarensis, Candida bromeliacearum, Candida carpophila, Candida carvajalis, Candida cerambycidarum, Candida chauliodes, Candida corydalis, Candida dosseyi, Candida dubliniensis, Candida ergatensis, Candida fermentati, Candida fructus, Candida glabrata, Candida guilliermondii, Candida haemulonii, Candida humilis, Candida insectamens, Candida insectorum, Candida intermedia, Candida jeffresii, Candida kefyr, Candida keroseneae, Candida krusei, Candida lusitaniae, Candida lyxosophila, Candida maltose, Candida marina, Candida membranifaciens, Candida mogii, Candida oleophila, Candida oregonensis, Candida parapsilosis, Candida quercitrusa, Candida rhizophoriensis, Candida rugosa, Candida sake, Candida sharkiensis, Aspergillus fumigatus, Aspergillus flavus, Cryptococcus neoformans, Cryptococcus laurentii, Cryptococcus albidus, Cryptococcus gattii, Histoplasma capsulatum, Pneumocystis jirovecii* (or *Pneumocystis carinii*) and *Stachybotrys chartarum*.

Where hospital-acquired or ventilator-associated pneumonia are concerned, the pathogens are gram-negative bacilli, *Pseudomonas aeruginosa, Klebsiella pneumoniae, serratia marcescens, Enterobacter, Citrobacter, Acinetobacter, Staphylococcus aureus* and antibiotic-resistant organisms such as methicillin-resistant *Staphylococcus Aureus* (MRSA). The above list represents over 80% of pathogens related to VAP.

Thus, in another of its aspects, the invention provides a method for determining presence of at least one pathogen in a subject's body (e.g., before symptoms associated with or indicative of the presence of the pathogen evolve or are apparent), the method comprising exposing to a breath sample at least one sampling unit comprising one or more adsorbing regions capable of reversibly associating to volatiles in said breath sample;

analyzing the at least one sampling unit to identify volatiles adsorbed onto the one or more adsorbing regions to determine presence of at least one pathogen-associated marker (or at least one marker associated with the pathogen), wherein the presence of said marker is indicative of existence of the pathogen in the subject's body.

In some embodiments, the pathogen is a virus, a bacterium or a fungus, as defined and selected herein.

In some embodiments, the subject is an asymptomatic subject, namely a subject not showing symptoms associated with the pathogen.

In some embodiments, the subject is a ventilated subject (a subject on a mechanical ventilation system). In some embodiments, the ventilated subject does not exhibit symptoms associated with VAP. In some embodiments, the pathogen is VAP causing, and is selected from any of the bacteria disclosed and known to cause VAP.

Thus, the invention also provides a method for determining presence of at least one pathogen in a ventilated subject's body (e.g., before symptoms associated with or indicative of the presence of the pathogen evolve or are apparent), the method comprising exposing at least one sampling unit to a breath sample from the ventilated subject, the at least one sampling unit comprising one or more adsorbing regions capable of reversibly associating to volatiles present in said sample;

analyzing the at least one sampling unit to identify volatiles adsorbed onto the one or more adsorbing regions to determine presence of said at least one pathogen-associated marker, wherein the presence of said marker being indicative of existence of the pathogen in the ventilated subject's body.

More specifically, the invention also provides a method for determining onset of VAP in a ventilated subject (e.g., before symptoms associated with or indicative of VAP evolve or are apparent), the method comprising exposing to a breath sample from a ventilated subject at least one sampling unit comprising one or more adsorbing regions capable of reversibly associating to volatiles in said breath sample;

analyzing the at least one sampling unit to identify volatiles adsorbed onto the one or more adsorbing regions to determine presence of at least one marker of a VAP-causing pathogen, wherein the presence of said marker is indicative of onset of VAP.

In some embodiments, a first breath sample is taken from the ventilated subject on day 0, namely on the day the subject is connected to the ventilation machine. In other embodiments, the first sample is taken at day 1, 2, 3, 4, or 5 from being connected to the machine and at any period thereafter (namely the second and further samples are taken hours or days after the first sample is taken).

In some embodiments, the at least one sampling unit is provided in a respiratory system typically used in ventilating the subject. Thus, in some embodiments, the method comprises exposing at least one sampling unit positioned at an outlet line of a respiratory system to a breath sample exhaled by the subject (e.g., an alveolar sample), the at least one sampling unit comprising one or more adsorbing regions capable of reversibly associating to volatiles present in said sample;

analyzing the at least one sampling unit to identify the volatiles adsorbed onto the one or more adsorbing regions to determine presence of at least one pathogen-associated marker, wherein the presence of said marker being indicative of existence of the pathogen-associated marker in the ventilated subject's body.

In some embodiments, the at least one sampling unit is in a form of a vessel comprising the one or more adsorbing regions and allowing a timed residence contact of the e.g., alveolar breath sample with the one or more adsorbing regions.

In some embodiments, one or both of the at least one sampling unit and the outlet line of the respiratory system is provided with a flow regulator (e.g., a valve).

In some embodiments, the disease-causing pathogen is a bacterium, a virus or a fungus, as defined and selected herein.

In some embodiments, the method further comprising detaching the at least one sampling unit from the outlet line of the respiratory system and analyzing same to determine volatiles adsorbed onto the one or more adsorbing regions.

In some embodiments, the volatiles adsorbed onto the one or more adsorbing regions are desorbed and thereafter analyzed.

In some embodiments, the method further comprising expositing at least one another sampling unit positioned at an inlet line of the respiratory system to ventilating air delivered to the subject.

In some embodiments, the analysis is carried out by a spectrometric method or a spectrophotometric method, as defined.

In some embodiments, the method further comprises comparing the materials adsorbed onto the one or more adsorbing regions to a database of marker materials to identify the material indicative of the presence of a disease-causing pathogen.

In some embodiments, the presence of the disease-causing pathogen is indicative of onset of a disease.

In some embodiments, markers identified in the exhaled air is compared to markers identified in inhaled air. Markers or materials that are exogenous, namely derived from the subject's surroundings, may be ignored or used as background in the analysis.

As used herein, the term "disease state" refers to a medical condition which diagnosis is desired utilizing a methodology of the invention. The presence of the disease state is typically concluded by determining the presence of a marker in a subject's breath sample that is associated with the metabolism, organ function, or presence and/or growth of a pathogen (e.g. bacteria, virus or fungus) that is involved in the pathogenesis of the disease state. The disease state is any disease identified by the WHO International Classification of Diseases. In most general terms, the disease state is any condition that can cause pain, dysfunction, distress, social problems, and/or death to the subject. Such states may be or may involve cardiac diseases, inflammation, renal diseases, cancers, pathogen-caused diseases and others. All these conditions are well known to a person versed in the art.

In some embodiments, the disease state is associated with a pathogen, as defined. In some embodiments, the disease state is associated with a bacterium. The disease states may be selected amongst those caused by the pathogens disclosed herein. Bacteria responsible for high infection morbidity and mortality include with a high tendency to be expressed in the lungs: Cholera (an acute infection of the small intestine caused by the *Vibrio cholera* and characterized by extreme diarrhea with rapid and severe depletion of body fluids and salts.); Diphtheria (caused by the *bacillus Corynebacterium diphtheriae* and characterized by a primary lesion, usually in the upper respiratory tract, and more generalized symptoms resulting from the spread of the bacterial toxin throughout the body); Meningitis (caused by *Neisseria meningitidis*; H. *Influenzae* occurs most often in infants and young children and only rarely in older persons; *Streptococcus pneumoniae* is a common cause of meningitis in adults. Various other strains of streptococci, pneumococci, staphylococci and tuberculosis can also cause meningitis); Tetanus (caused by toxins produced by the *bacillus Clostridiun tetani* and characterized by rigidity and spasms of the voluntary muscles); Lyme disease is caused by several closely related spirochetes, including *Borrelia burgdorferi* in the United States, *B. mayonii* in the upper Midwestern United States, and *B. afzelii* and *B. garinii* in Europe and Asia. The spirochetes are transmitted to the human bloodstream by the bite of various species of tikes); Syphilis—a systemic disease that is caused by *Treponema pallidum*. Syphilis is usually an STD (sexually transmitted disease), but it is occasionally acquired by direct nonsexual contact with an infected person, and it can also be acquired by an unborn fetus through infection in the mother.

In some embodiments, the pathogen-caused disease is a hospital acquired infection. In some embodiments, the pathogen-caused disease state is VAP or hospital-acquired pneumonia.

In some embodiments, the disease state is cancer. Non-limiting examples of cancers include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma. Also included are breast cancer, lung cancer, colorectal cancer, prostate cancer, ovarian cancer, endometrial cancer, gastric cancer, clear cell renal cell carcinoma, glioblastoma, uveal melanoma, multiple myeloma, rhabdomyosarcoma, Ewing's sarcoma and medulloblastoma.

In some embodiments, the disease state is a disease of the liver or kidneys.

In some embodiments, the disease is associated with the lungs. Non-limiting examples include bronchiectasis, emphysema, chronic bronchitis, chronic obstructive pulmonary disease (COPD), asthma, pneumonia, pleural effusion (PE) and ventilator-associated pneumonia (VAP), cystic fibrosis, ARDS (acute respiratory distress syndrome), smoking, asbestos, and others.

Wherein reference is made to an asymptomatic subject, the subject is regarded, as explained herein, as not exhibiting any one symptom known to be associated with the disease state. In some cases, the invention contemplates detecting a cause of a disease in subjects that are asymptomatic or at an early stage of a disease before symptoms are apparent or before the subject has undergone medical examination or tests that identified a medical condition. For example, in the case of ventilated subjects attracting VAP, detection of the pathogen is desired in the ventilated subject not showing symptoms associated with the infection, namely at a stage before symptoms such as fever or low body temperature and hypoxemia occur. Thus, the "onset of a disease state" refers to the subclinical stage of the disease, showing no signs and symptoms that are detectable by physical examination or laboratory test. More specifically, the onset of a pathogen-caused disease refers to the incubation period and in some cases to the prodromal period, as known in the art.

Also, a "diseased state" or early detection of a disease onset may be regarded as the point when any growth in the marker concentration is measured overtime. Such a growth is directly associated with a bacterial mass or a viral load indicative of the diseased state. As noted herein, wherein a certain marker is indicative of the presence of a microorganism typically present in a subject microbiome, the onset point would be regarded when the marker level is increases or at least, compared to a background level; namely compared to a level measured at a first instance or at an earlier time point.

The present invention is further directed to a method for determining a disorder or a disease in a patient being ventilated, the method comprising:

contacting at least one collecting or sampling unit equipped with a valve and comprising an adsorbing material to an outlet and/or an inlet line(s) of a respiratory system to capture by adsorption volatile and semi-volatile compounds present in an exhaled and/or an inhaled air passing into the collecting unit upon opening of the valve, wherein the valve is situated between the inlet and outlet lines and the at least one collecting or sampling unit, thereby allowing the compounds present in the air passing through the collecting or sampling unit to adsorb to said adsorbing material;

desorbing the compounds adsorbed in the at least one collecting or sampling unit and transferring for analysis;

providing an analytical unit for chemical identification of the desorbed compounds and optionally determining the relative amounts of each of the detected compounds;

providing an analyzing system for initially creating a first list of compounds including the relative amounts of each of the detected compounds, wherein the analyzing system further comprises a database for further analysis of the identified compounds.

In some embodiments, the valves are opened several times a day, each time for a certain period of time for allowing exhaled and/or inhaled air to pass through the at least one collecting unit. The duration of each opening and the number of times the valves are opened may be predetermined or done upon need.

The invention further provides a method for determining success of a medical treatment of a subject under medical treatment, the method comprising exposing at least one sampling unit comprising one or more adsorbing regions capable of reversibly associating to volatiles in a breath sample from the subject and permitting the volatiles in said breath sample to adsorb to said one or more adsorbing regions;

analyzing the at least one sampling unit to determine presence and/or amount of a marker indicative of the disease, wherein the presence or absence of said marker and/or a change in the amount of said marker relative to an amount measured at an earlier time point provides an indication of success or failure of the medical treatment.

As used herein, the medical treatment may be any such treatment aiming at ameliorating undesired symptoms associated with a disease, preventing the manifestation of such symptoms before they occur, slowing down the progression of the disease, slowing down deterioration of symptoms, enhancing the onset of a remission period, slowing down irreversible damage caused in a progressive chronic stage of the disease, delaying onset of said progressive stage, lessening severity of the disease, curing the disease, improving survival rate or more rapid recovery, or preventing the disease form occurring. While a successful medical treatment may be regarded in achieving any of the aforementioned aims, in accordance with methods of invention, a successful medical treatment may be regarded in one or more of the following: (1) where the marker is no longer detected in the subject's breath sample; (2) where the amount of the marker is reduced over time; (3) where the amount of the marker is reduced relative to another marker present in the breath sample; (4) reduction of clinical signs and symptoms related to the diseased state as determined following the initial identification through the proposed invention.

Any of the methods disclosed herein may comprise a step of treating a subject identified as having a disease or a condition to prevent the further progressing of the disease or condition. The treatment may involve administration of an active material or of a treatment protocol intended to ameliorate symptoms that may be associated with a disease or prevent manifestation of such symptoms before they occur, slow down the progression of the disease or condition, slow down deterioration of symptoms that may occur, slow down irreversible damage that may be caused in a progressive chronic stage of the disease or delay onset of the progressive stage, lessen severity of the developing disease or condition, improve survival rate, or prevent the disease form occurring.

The invention further provides an apparatus, a device or a system for carrying out methods of the invention. The apparatus, device or system is generally provided with at least one sampling unit comprising one or more adsorbing regions capable of reversibly associating to volatiles in a breath sample from the subject, as disclosed herein, wherein the at least one sampling unit is optionally detachable from said device and may be separately handled. One such device is a respiratory system as disclosed herein.

Where the sampling unit is detachable from the device, it may be manually or automatically removed for analysis, e.g., at a different location. Analysis may be achievable on site as well. In cases where the sampling unit is not detachable or in case it is not configured to stand as a separate modality from the device, the sampling unit may be provided with an opening enabling communication of the breath sample thereinto and an opening enabling removal of the volatiles after desorption for direct analysis. In some cases, the unit comprises a single opening meeting both purposes. In other embodiments, the sampling unit comprises two more openings. Each of the openings may be provided with a valve or valve assembly.

Also provided is a sampling unit comprising at least one adsorbing region, the region being formed of a porous material or a plurality of functionalities capable of trapping or associating to volatiles in a breath sample, as disclosed herein. In some embodiments, the sampling unit has an opening configured and operable to permit flow of a breath sample thereinto. The opening may be adapted with a valve unit enabling control of material flow into and out from the unit. The unit may further optionally comprise or be provided with a means or a port adaptable to tightly associate to a device or a system.

The invention also provides a respirator system comprising a compressible air reservoir, a set of tubes and a patient circuit comprising an inhaled air tube and an exhaled air tube, the patient circuit being connected to a tracheal intubation tube, one or both of the inhaled air tube and an exhaled air tube being provided with at least one sampling unit positioned in a path of an alveolar breath exhaled by a ventilated subject, the at least one sampling unit comprising one or more adsorbing regions capable of reversibly associating to at least one volatile material present in said exhaled alveolar breath and indicative of a disease state or a presence of a disease-causing pathogen.

Also provided is a system configured for determining presence of a disease-causing pathogen in a ventilated subject, the system comprising a ventilation apparatus comprising a patient circuit provided with a plurality of optionally detachable collecting surfaces positioned in a path of exhaled air, each of said plurality of collecting surfaces being characterized by a plurality of binding regions, each of said binding regions being in a form of binding molecules and/or surface features and configured to reversibly associate to at least one material indicative of the presence of the pathogen.

Any of the methods or systems of the invention, may rely to some extent on an early knowledge and understanding of the markers which presence in a breath sample defines, e.g., onset of a disease or presence of a certain pathogen. Characterizing features that, inter alia, differentiate one disease over the other, that define an onset of a disease state and that define a proper evolution of a successful medical treatment are also of importance. While the majority of markers that find their way into the breath of a subject and which are known to evolve with or to be caused by a disease or a microorganism, and thereby are indicative of the disease state and presence of the microorganism, are known. Determining association between such disease states or pathogens with markers that can be detected in a breath of a subject may be achieved by methodologies known in the art. Such methodologies may involve collecting markers from a headspace above abnormal cells or pathogens in a sealed vessel or determining the identity of the markers in blood or other body fluid samples.

With the disease-specific or pathogen-specific markers known, data obtained from certain methods of the invention may be compared to data collected and stored in a database. For example, in determining success of a medical treatment or in determining whether a change in a specific marker fingerprint is indicative in an early evolution of a disease state, the marker and the marker concentration or amount or level measured in the breath sample may be compared to a control. The control refers to any component of a marker fingerprint obtained from subjects not having the disease, namely subjects who have been tested and found not to have been affected by the disease, or known to be free of the disease, as well as from subjects who are suffering from the disease. These may be used to define a "healthy group" namely a group of subjects who do not have the disease, and a "sick group", namely a group of subjects who are suffering from the disease. When comparing the marker fingerprint to a marker profile of a control, a determination can be made whether the fingerprint is indicative of a subject that has contracted the disease or the pathogen or of a subject who has not. In a similar fashion, to enable a diagnostic determination as to whether a medical treatment is successful, the marker fingerprint taken from the subject may be compared to a control sample(s) obtained from the same subject at one or different time points prior to or after treatment has commenced.

Control samples obtained for the purpose of determining the presence or absence of a disease are typically taken from a plurality (one or more) subjects which have been identified as healthy or as sick. The number of subjects may be between at least 10 to thousands of subjects.

As noted therein, a change in the VC profile and its evolution over time, e.g., as compared to a control, may be determined by utilizing an algorithm such as, but not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA) or cluster analysis including nearest neighbor.

The control data may be stored in a database that compiles qualitative and quantitative lists of grouped compounds previously determined to indicate as markers of a disease or a pathogen, as disclosed. The database may further comprise a marker combinations or fingerprints, with each being attributed to a specific identified pathogen, e.g., bacteria or disease state.

As used herein, a group of markers which provide a predictive indication for the possibility of a diseased state or presence of a pathogen is regarded as a fingerprint or a cluster. Different microbiomes produce different clusters. Thus, detection of a specific cluster or fingerprint may define a microbiome. In addition to the list of molecules contained in the fingerprint, an algorithm analyzes a change in concentrations and the relations between the markers to define a change (positive or negative) in cluster content and/or concentration between consecutive patient samples. The algorithm is also set to define a rate of change in cluster parameters ("gradient"), a change that can determine the onset of a disease, disorder or condition and hence the need and urgency of reporting to a medical staff. Rate of increase (gradient) in levels of cluster components may also attribute to the seriousness of the threat. Gradient defines trends in composition and not only trend in a specific molecule.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 9A-9E provide detection of bacterial load by detecting "fingerprints" (cluster of compounds) that were previously found to be characteristic of a certain bacterium.

FIGS. 11A-11D provide detection of bacterial load by detecting specific single compounds that were previously found to be characteristic of a certain bacterium.

FIGS. 12A-12E provide a method by which the concentration of a specific compound (1-ethyl-4-methyl-benzene—FIG. 11B) is determined in exhaled air.

DETAILED DESCRIPTION OF EMBODIMENTS

Figure 1:
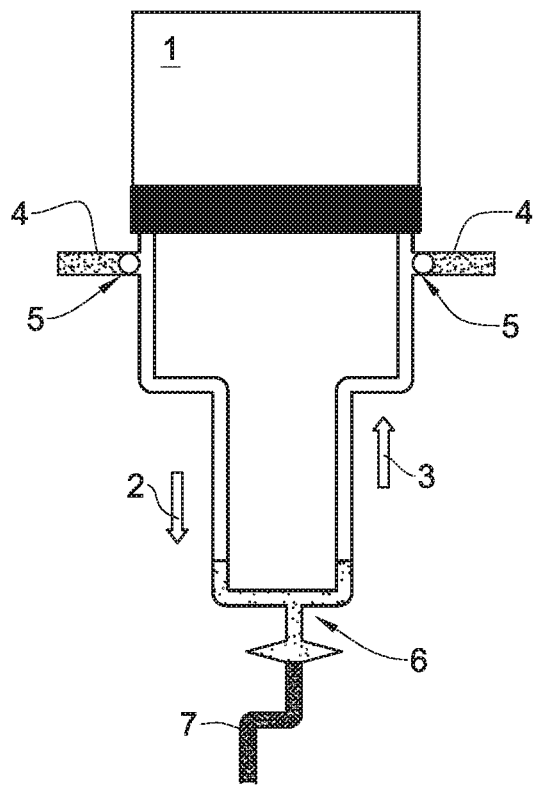
FIG. 1 is a schematic representation of a mechanical ventilator (MV) showing several locations of a sampling or collecting units in accordance with embodiments of the invention.

The present invention is directed to methods and systems as disclosed herein.

For the purpose of demonstrating the uniqueness of the technology, a complex medical condition was chosen as a test. VAP involves a pathogen, a subject who is typically uncooperative, who has an existing active medical condition and a potentially evolving life-threatening disease which early detection is highly sought for. Thus, the examples provided herein demonstrate the capabilities of the technology disclosed herein in (a) early detection of a pathogen (before symptoms associated with the pathogens are apparent), (b) the ability to detect the pathogen or disease at an early stage and prevent its development and complications that may be fatal if not detected at an early stage, (c) detection of a pathogen in a subject already suffering from an active disease, (d) the ability to distinguish between markers associated with the pathogen and other illness-causing factors, (e) in collecting samples from a subject who is uncooperative, (f) the ability to monitor treatment and relate it to the levels of markers, [i.e., decrease in marker levels may be related to decrease in pathogen activity (effectiveness of treatment). In contrast, increase of marker levels under treatment may indicate that treatment is not effective and there is need to change treatment (use of antibiotics, use of different antibiotics, physical therapy, positional changes etc.)], (g) periodic scanning of mechanical ventilators for contaminants, (h) compare marker levels in all mechanical ventilators (MV) in an ICU unit and detect contamination with endemic bacterium; and others.

Thus, methods of the invention aim at providing a method for early detection of a bacterial condition, disease or disorder in a subject; a method for determining onset of a bacterial condition, disease or disorder in a subject; a method for preventing development or delaying the progression or onset of a bacterial condition, disease or disorder in a subject. These methods are conducted according to the present invention by sampling exhaled air coming out of a subject; sampling being performed by adsorbing materials/compounds that are present in the exhaled air, desorbing the adsorbed material/compounds, analyzing them and comparing them to a predetermined known database that contains information pertaining to such material/compounds that are discharged by bacteria to their surroundings.

The present invention is also directed to a system for accurate and quantitative determination of compounds present in exhaled and/or inhaled air from the respiratory system of a living animal, preferably a mammal, preferably human. These compounds are volatile and semi-volatile compounds (VOC, sVOC), preferably organic compounds. The system detects such compounds by sampling air exhaled and inhaled from the human lungs and adsorbs the compounds present in the air while the sampled air passes through appropriate units that comprise appropriate sorbents that adsorb these compounds in a manner that preferably does not alter their chemical properties and structure. Such sampling requires considerable amounts of air to pass through the appropriate units and hence according to the present invention the system may be used in patients being mechanically ventilated such that the pressure exerted by the ventilator provides deriving force for allowing sufficient amount of exhaled and/or inhaled air to be sampled. Passive sampling is also possible, for example taking an air sample of air exhaled from the nose to prevent sampling the bacterial/viral/fungal population in the mouth.

The compounds adsorbed on the sorbents of the appropriate units are usually desorbed by heating to a temperature above the boiling points of the adsorbed compounds, yet below the temperature the sorbent begins to break down chemically. The desorbed compounds are transferred to analytical unit that separates and identifies the compounds. By identification it is meant identifying both the chemical nature and chemical properties of these compounds, their grouping, such as alkyls, alkenes, alkynes, alcohols, amines, aromatic, cyclic, heteroatoms such as P, N, O, S, present in any of the above groups, and their relative amounts in the sampled air. A further analysis system receiving the data identified by the analytic unit and provides a chemical picture, i.e. a list of the compounds that were detected and identified and provides an indication of compounds that are present in the respiratory system of the individual whose air is sampled.

This obtained list of compounds includes numerous compounds and their intensities, and their connection to a disorder or a diseased stage is not straightforward and should be elucidated. For such elucidation the present invention makes use of two other features present in the analysis system. The two other features are a unique database and unique algorithms; both are part of the present invention.

The unique database includes data that were previously obtained that include lists of grouped identified compounds discharged to the surroundings by bacteria where the volatile and semi-volatile compounds produced and discharged to the surroundings of the bacteria were captured, identified and serve as a base for comparison. Each bacterium discharges its own unique compounds at certain relative amounts and the entire list of compounds is the "fingerprint" of this particular bacterium that includes biomarkers. The biomarkers serve for analysis according to the present invention.

The unique algorithm of the present invention compares between the groups of biomarkers being a cluster of biomarkers present in the database and the compound, or compounds that are identified in the exhaled air. Hence a match between the compound obtained by the analyzed sampled air of the individual and the clusters in the database serves as an indication of the presence of the particular microbiome indicative of a certain bacteria in the respiratory system of the individual and hence the disorder or disease associated with such bacteria is identified.

The background compounds that are present in the respiratory system of the individual originating from the surroundings of the individual and the apparats in his vicinity may be or may not be taken into account (by means of subtracting background). These include compounds present in the source of air of the ventilator system, the microbiome of the specific hospital, clinic the individual is placed in and compounds discharged by medical equipment in the individual surroundings. These compounds will enter the respiratory system through the air incoming into the lungs and hence sampling the air in the inlet tube of the ventilator, elucidating the compound(s) as done for the exhaled air and subtracting it from the compound(s) present and identified in the exhaled air that may provide a cleaner picture of the compounds that originate in the respiratory system due to a disorder or a disease.

The present invention thus demonstrates and exemplifies a relevant portion of the group of compounds discharged by various bacterium, identifying the nature and relative amounts of the compounds that are produced by these bacterium and produce the list of various specific compounds that are indicative of the existence of these bacteria in the air that is sampled. These compounds are termed target molecules and are indicative of this specific bacterium. The group of compounds and their relative amounts are indicative of a certain bacterium (or bacteria) and therefore serve as biomarkers unequivocally identifying the bacterium or bacteria. According to the present invention, identifying biomarkers of one or more bacterium in the exhaled air in a certain measurement and an increase in its concentration relative to a previous measurement is indicative of the disorder, condition or disease that is known to be associated with this specific identified bacteria. Identifying the biomarkers of one bacterium or a cluster of biomarkers, that is a group of more than one biomarker, are indicative of a disorder, a conditioned or a diseased state.

It should be understood that each bacterium is identified by its characteristic compounds. A certain bacterium at a given situation may produce and discharge to its surroundings one or more compounds where the compound or compounds that is/are produced and discharged vary in their amounts when comparing one bacterium to another different bacterium. Overlap of single (one or more) of compounds discharged by two different bacterium is frequently found, however, the complete identified spectra of a specific, well identified bacterium is different than that of another bacterium by the fact that the quantities and entire list of compounds of the specific bacterium are different than another bacterium. Further, each of the compound(s) produced and discharged is/are identified in the analytical system by its retention time (RT). Calculating the relative retention times (RRT) for each set of compounds discharged from a specific bacterium provides more a accurate evidence of a specific bacterium. Therefore mere identification of compounds, let alone one compound in the air sampled from the respiratory system of an individual is not sufficient for identifying the presence of a certain bacterium since different bacterium may produce and discharge to the surroundings the same compound (albeit at different concentration).

The present invention is thus directed to identifying diseases and disorders that are associated with bacterial infection allowing to collect volatile and semi-volatile compounds discharged to the surroundings of bacteria by the bacteria, identify these compound, their intensities, and compare these with a database that includes previous collect data on nature of compounds discharged by known bacteria and the intensities of each such compound.

In particular, the present invention is directed to identifying disorders, diseases or conditions associated with the lungs, non limiting examples being Bronchiectasis, Emphysema, Chronic Bronchitis, Chronic Obstructive Pulmonary Disease (COPD), Asthma, Pneumonia, Pleural Effusion (PE) and ventilator-associated pneumonia (VAP).

Figure 2:
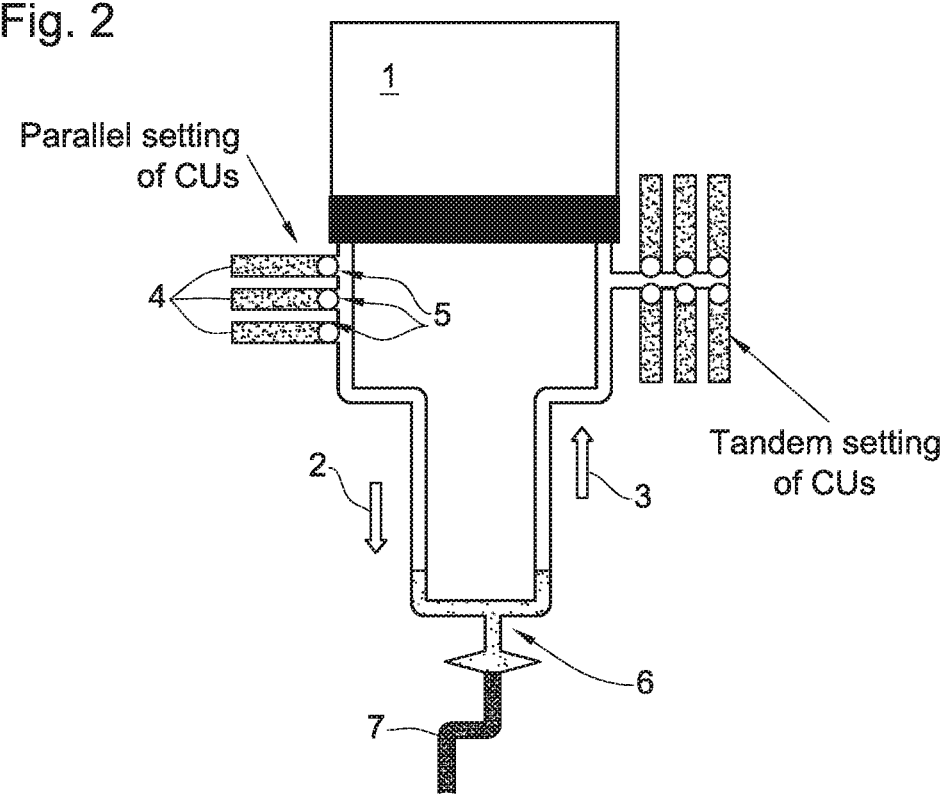
FIG. 2 is a schematic representation of a parallel and a tandem arrangement of a mechanical ventilator (MV) showing several locations of several sampling or collecting units according to certain embodiments of the invention.

FIGS. 1 and 2 schematically depict a mechanical or any other type of a ventilator unit 1. According to a proper operation of the unit, air is forced from the unit through an inhaling tube 2, in the direction shown by the arrow, and the intubation tube 7 to the patient's lungs. Compounds present in the lungs, preferably volatile organic compounds (VOC's), markers, are taken with the exhaled air from the lungs through the intubation tube 7 and exhale tube 3, in a direction shown by the arrow. The exhaled air is moved out of the lungs either passively or due to pressure exerts by the unit on the breathing system of the subject. Alternatively, it may also be moved out by a pump. One or more sampling units 4, optionally equipped each with a valve 5 or a T-shaped connection, are installed in either or both the inhale 2 and exhale 3 tubes where they passively and/or actively adsorb VOCs.

In some cases, location of the one or more sampling units 4 may be inside the inhale and/or exhale tubes and/or perpendicular to the inhale and/or exhale tubes. When located perpendicular to the inhale and/or exhale tubes, the location is typically at a distance of 1-200 cm, 1-20 cm, 10-60 cm, 50-100 cm, 100-150 cm or 150-200 cm from the bifurcation 6 that separates the inhale tube from the exhale tube. The number of units in the inhale and/or exhale tubes may vary and can be one or more per inhale or exhale tube.

Location of the sampling unit perpendicular to the inhale or exhale tube is typically at a distance of between 1-50 mm, 1-30 cm, between 1-20 cm, between 1-10 cm or between 1-5 cm from the flow to minimize the Venturi effect and the resulting turbulence in the sampling unit. A flow-limiter (not shown) may be located at the distal end of the unit to control flow rate, increase VOC uptake, minimize fluctuations and, thus, provide high repeatability. The valves 5 which are optional (and are for illustration only) are positioned close the connection to the inhale tube 2 or exhale tube 3 when the unit 4 is not connected or is detached. Any other means such a T-shaped connector which tip is closed when the unit is shut, is also possible.

In FIG. 1, a single sampling unit 4 is shown that is positioned perpendicular to tube 2 and a single unit is positioned relative to tube 3. In FIG. 2, a plurality of sampling units is shown, grouped equally at each tube 2 and 3. The number of sampling units may be one or more, wherein the units may be positioned at the inhale tube 2 or the exhale tube or on both. Typically, at least one sampling unit is positioned at the exhale tube 3. In cases where the number of tubing is greater than 1, namely two or more, and in cases where two or more sampling units are positioned at the exhale tube or the inhale tube, the units may be arranged in parallel or in tandem, as shown in FIG. 2. While a parallel setting is shown positioned at the inhale tube and a tandem setting at the exhale tube, this is not limiting and any combination of setting for each of the inhale and exhale tubes may be used.

Figure 3:
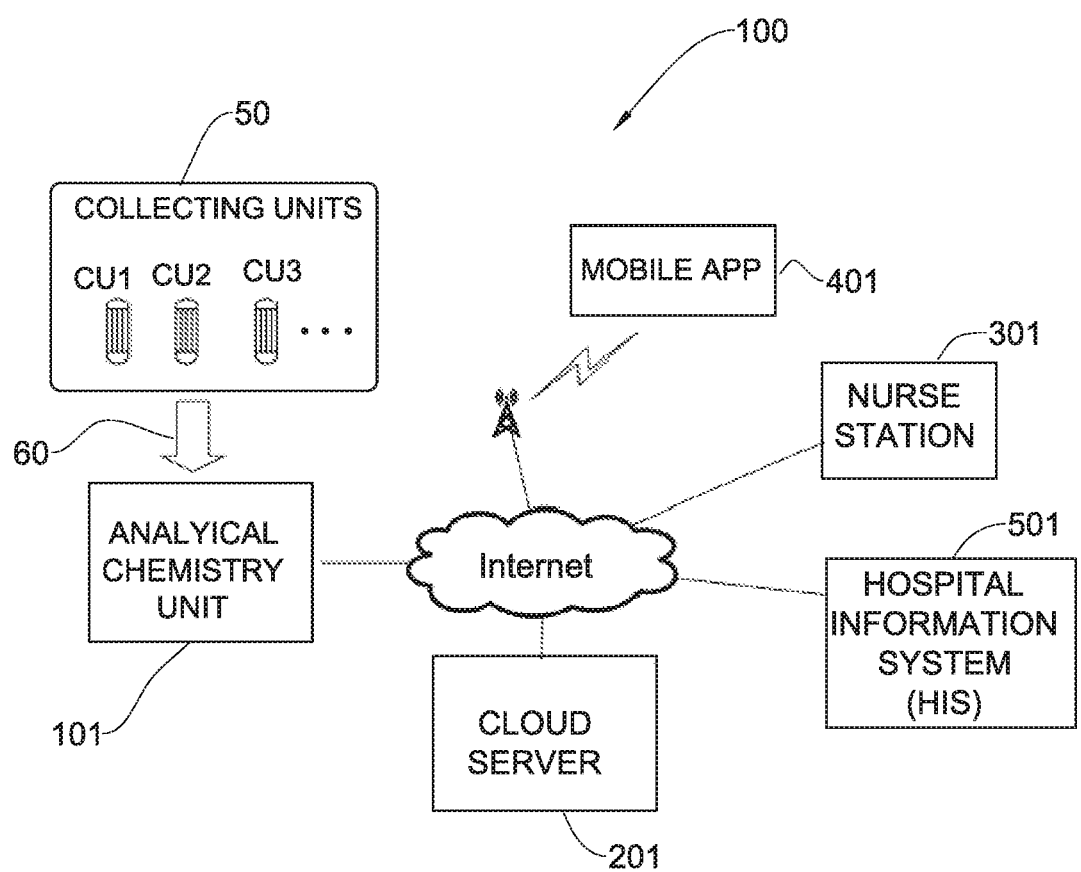
FIG. 3 is a schematic drawing of an exemplary VADS (Ventilated Associated Detection System) of the invention, where a single analytical chemistry unit is deployed, being processed in the cloud server and provides a patient's status in different forms.

Turning to FIG. 3, a ventilated associated detection system (VADS) 100 is shown. The system comprises of a plurality of sampling units labeled (as Collecting units) CU1, CU2, CU3 . . . etc, (50) which chemical contents is transferred by a sample connection that may be an autosampler (60) to an analytical chemistry unit 101. Data obtained from the analytical chemistry unit 101 is delivered to a central server (not shown) or a cloud server 201. At the central server/cloud—data is inserted to analysis algorithm and compared to metadata bank and to patient's previous samples. The metadata bank includes sets of 'clusters' being several VOC's which are specific to a particular disease or pathogen (determined in accordance with the present invention). The 'clusters' may be also sub-classified to a specific pathologic agent (e.g., to a specific bacterium causing the disease) or to a specific sub-population of patients (e.g., a group of diabetic patients with VAP). The metadata also includes data on the patient and data base on known microbiomes and the hospital's microbiomes which may also be used in assessing the patient's condition. Algorithm(s) determine statistical probability for change is patient's status that may indicate the onset of an infection, cardiovascular status, nutritional status, cancer status and reports said to staff. "Change" implies a pre-determined gradient (change) in concentration of cluster elements over a number of successive sampling events. The output is in turn delivered for further action/treatment or for storage. The output may be subsequently delivered to a nurse/doctor's station 301, a mobile application 401, a hospital information system 501 and to others.

Figure 4:
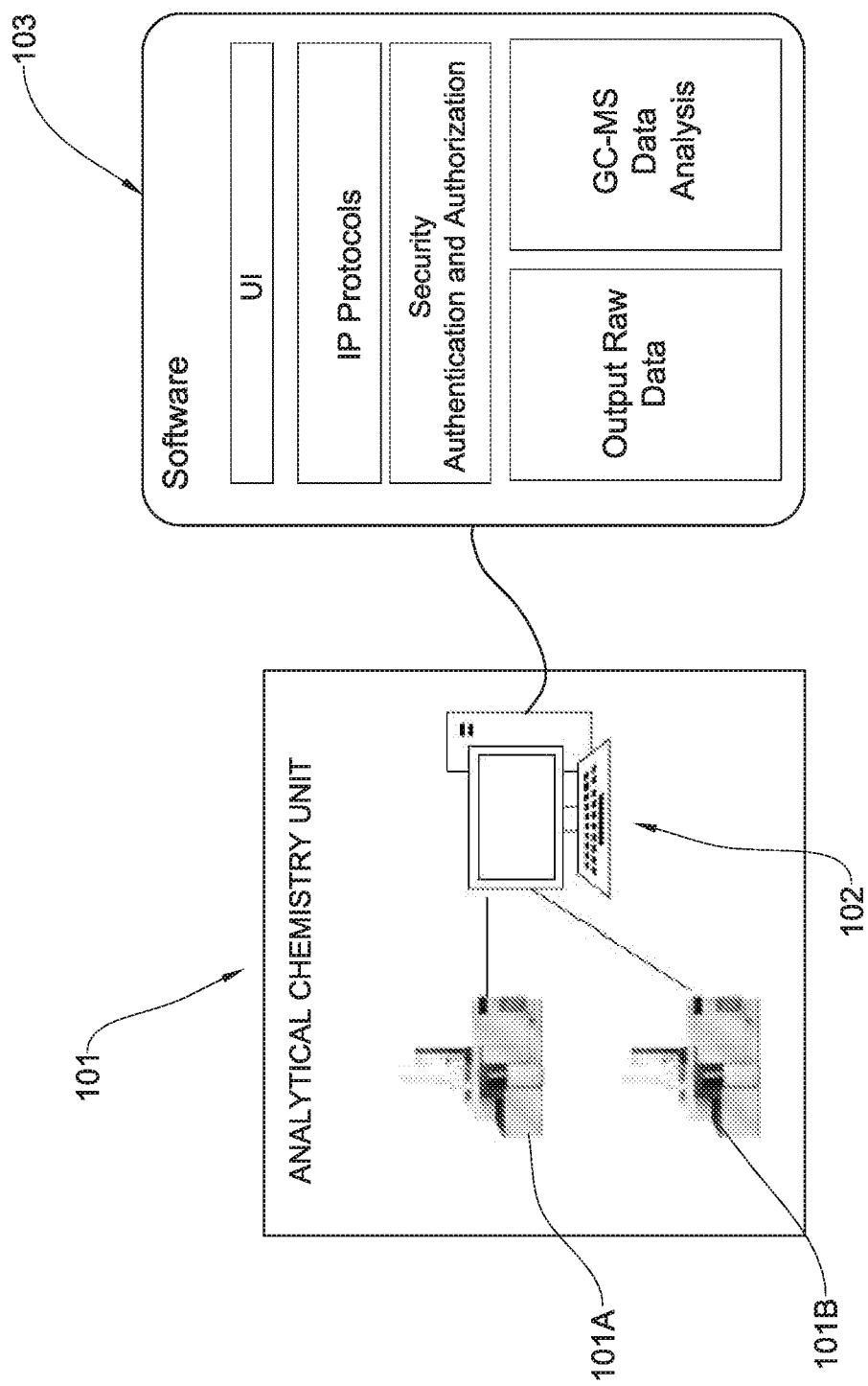
FIG. 4 is a schematic representation of an analytical chemistry unit used by the present invention.

In FIG. 4 an analytical chemical unit 101 is provided. It includes one or more GC-MS instruments such as 101A and 101B connected to a PC 102 and running a software illustrated in 103. The contents of the collecting units 4 (shown in FIGS. 1 and 2) that contain patient's samples, is being fed to the GC-MS via an autosampler for digital conversion and generating of digital raw data. The GC-MS output raw data is processed in the data analysis software entity and patient specific data measurement is provided, which is packed, encrypted and sent over the internet network using an IP protocol. The packed data includes the current measurement as well as the patient ID, time stamp and/or other related information. The user interface (UI) provides the technician with the ability to monitor and control the GC-MS operation as well as monitor and control of the analysis process.

Figure 5:
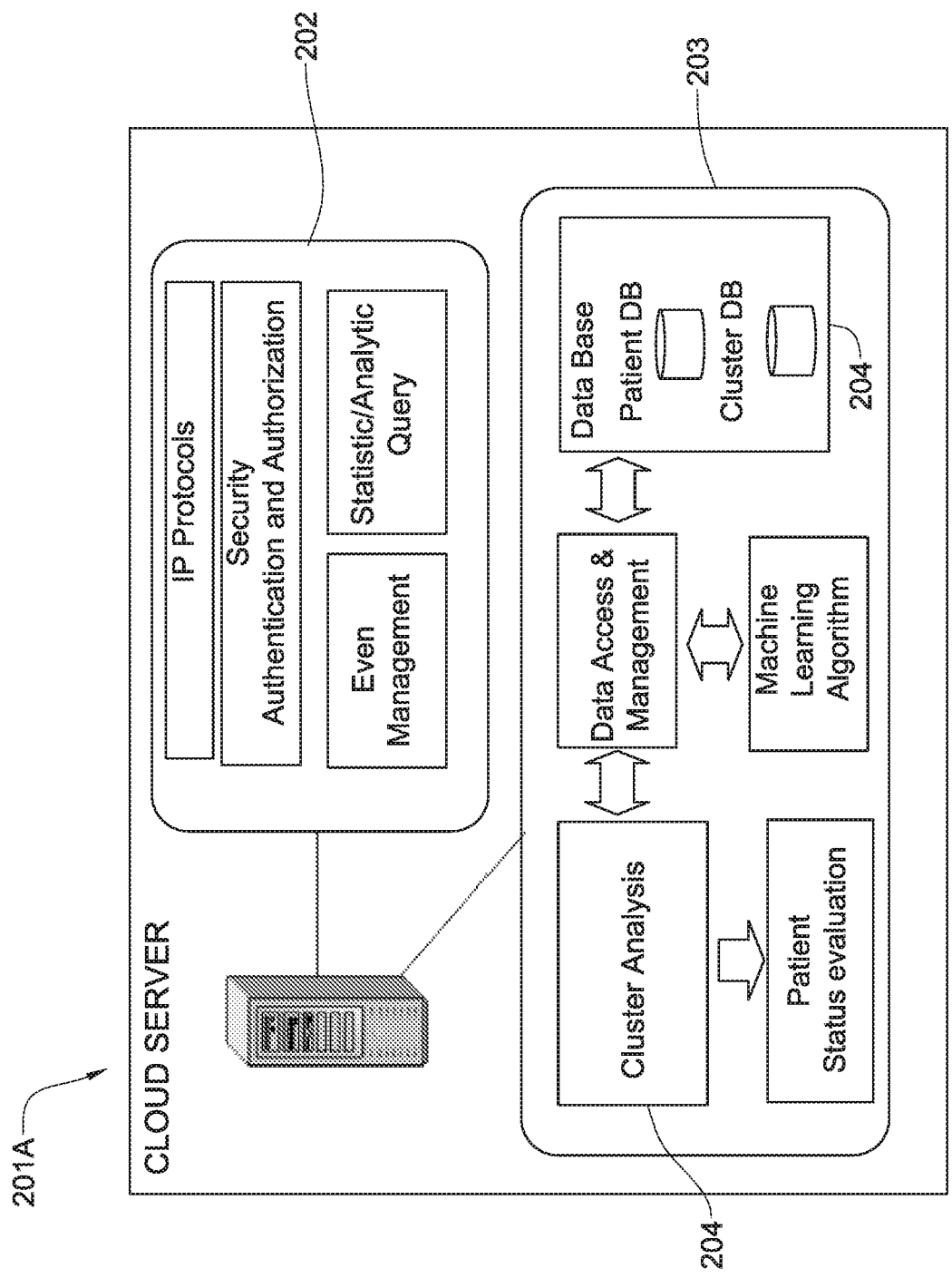
FIG. 5 is a schematic representation of a cloud server sub-system for data analysis.

In FIG. 5 a cloud server subsystem is shown in 201A. The cloud server receives and manages information from multiple analytical chemistry units deployed in the system. A non-limiting embodiment of the present invention provided in this figure is the division of the system into two main groups 202 and 203. System 202 includes the software includes the IP protocols that send and receive information between the cloud to the chemistry units and remote stations, and the security and authorization entity which encrypt and decrypt each patient data and provide the authorization for accessing the information. It also includes the cloud server event management entity. These may include new data that is received, patient alarm, failures indication or any other system events, and statistic/analytic query for inquires required by user and/or other software entities. System 203 includes the main software processing related to this invention. The cloud server data base 204 comprises patient data base, storing measurement history from specific patients taken in different time interval, and cluster data base related to specific molecules signals characteristic which is used for the prediction of a specific disease. The data access and management software entity is the interface to store and retrieve data from the relevant data base. The cluster analysis software algorithm is getting new measurement from the patient, compare and process it with information retrieved from the cluster data base and previous patient measurements. The patient status evaluation algorithm software is responsible to predict patient disease of specific type and/or indication of treatment effectiveness and/or generate an alarm for one or more of the remote stations. The algorithm determines the level of change between consecutive measurements from the initial patient baseline when patient arrives to the ICU to the latest, and based on the gradient characteristic providing the status of patient and statistical prediction of specific disease and the effectiveness of treatment given based on early detection. A Machine Learning (ML) algorithm entity is used for continuous improvement of the prediction made based on the gradient measurement using the entire patient's history data collected in the system. It is used for improvement of the statistical false alarm and misdetection of the system over time.

Figure 6A:
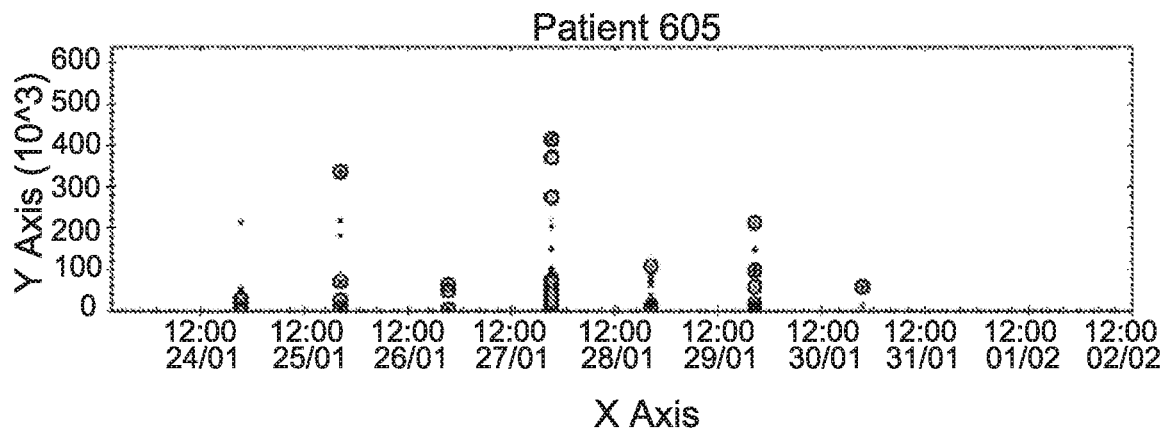
FIG. 6A provides a computerized output of a GC-MS raw data after processing in a data analysis software entity.
Figure 6B:
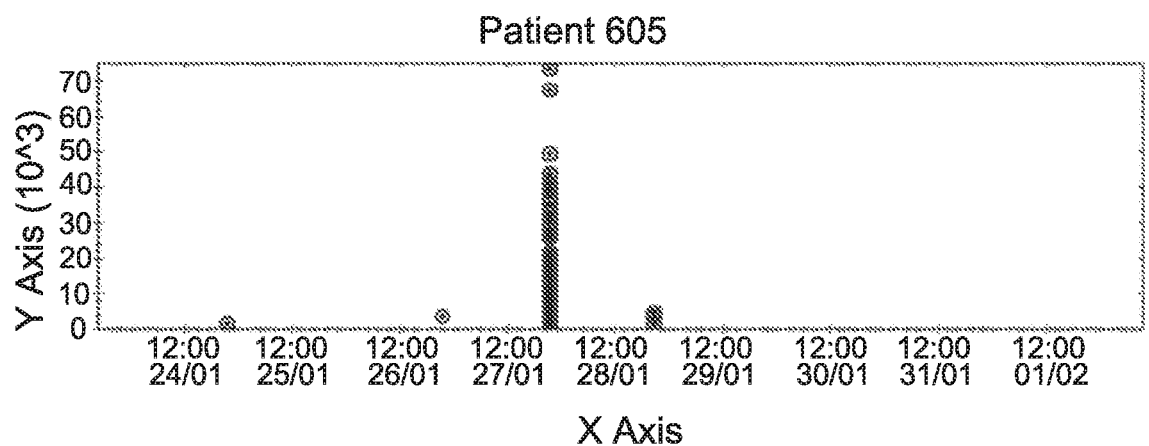
FIG. 6B provides an enlarged picture of a particular target molecule indicative of the presence of a certain bacterium in an exhaled breath of a patient.
Figure 6C:
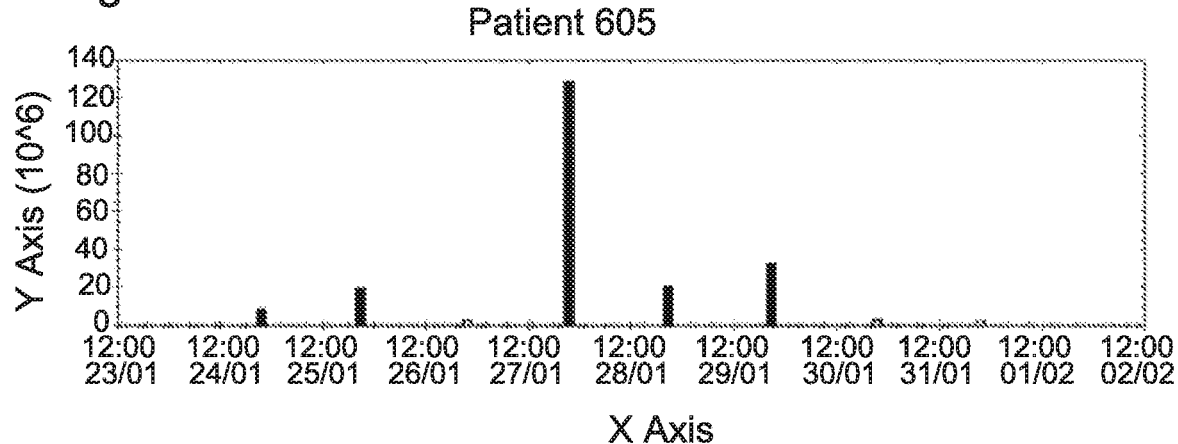
FIG. 6C provides the bacterial load of a patient showing characteristic markers indicative of the microbiome.

FIG. 6A demonstrates a computerized output of a GC-MS raw data after its processing in the Data Analysis software entity, generating patient specific data measurement. FIG. 6B provides an enlarged image of a particular target molecule indicative of the presence of a certain bacterium in an exhaled breath of a patient. FIG. 6C provides the bacterial load of the patient, showing characteristic target molecules of the microbiome of the patient.

Figure 7A:
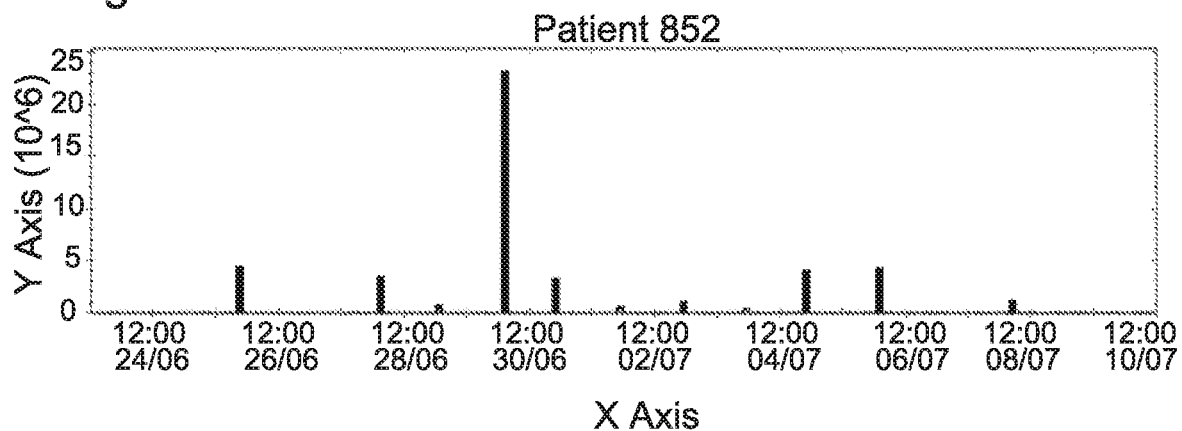
FIGS. 7A-7C provide bacterial load of Staph (MRSA), *Acinetobacter* (9) and *Klebsiella*, respectively of a patient.
Figure 7B:
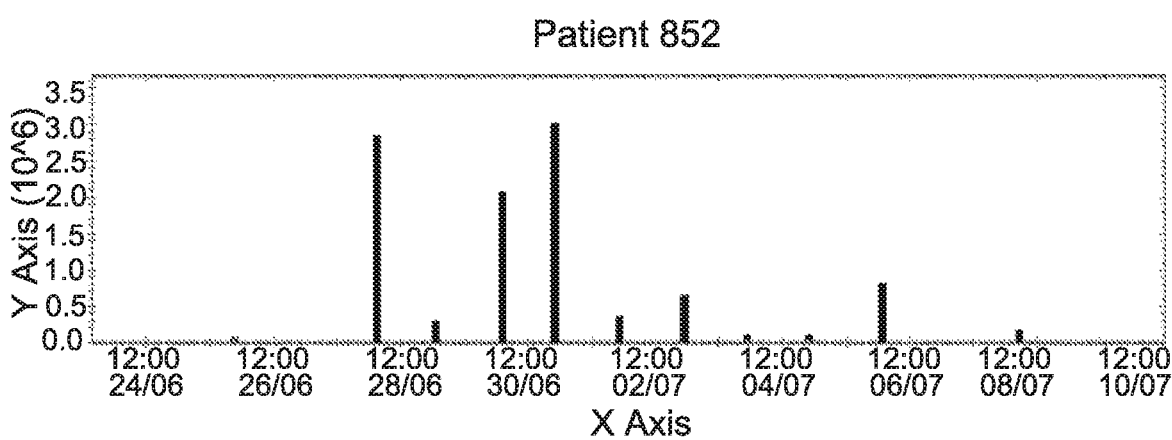
Figure 7C:
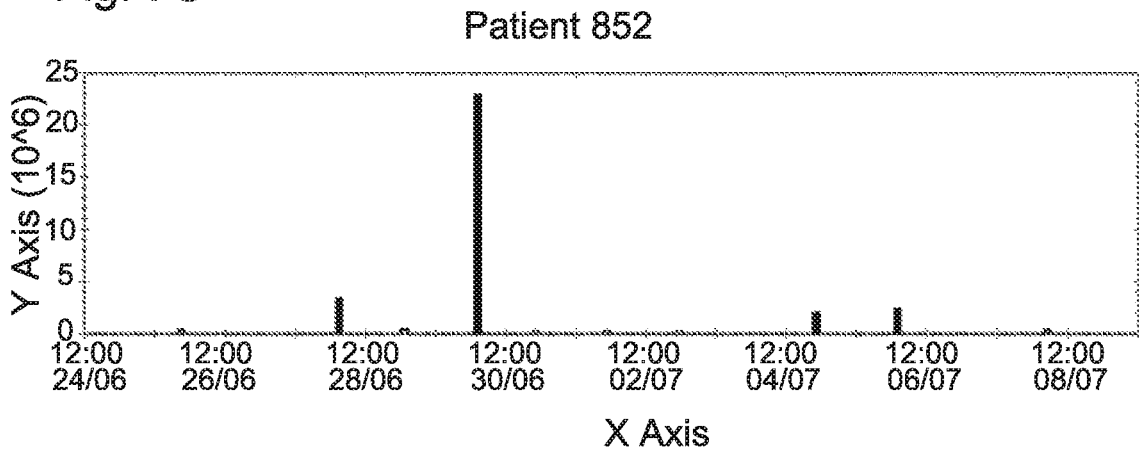

In FIGS. 7A, 7B and 7C, the bacterial load of three known bacteria in a certain patient diagnosed according to the present invention are displayed. In particular, Staph (MRSA), *Acinetobacter* (9) and *Klebsiella*, respectively, are demonstrated.

Figure 8A:
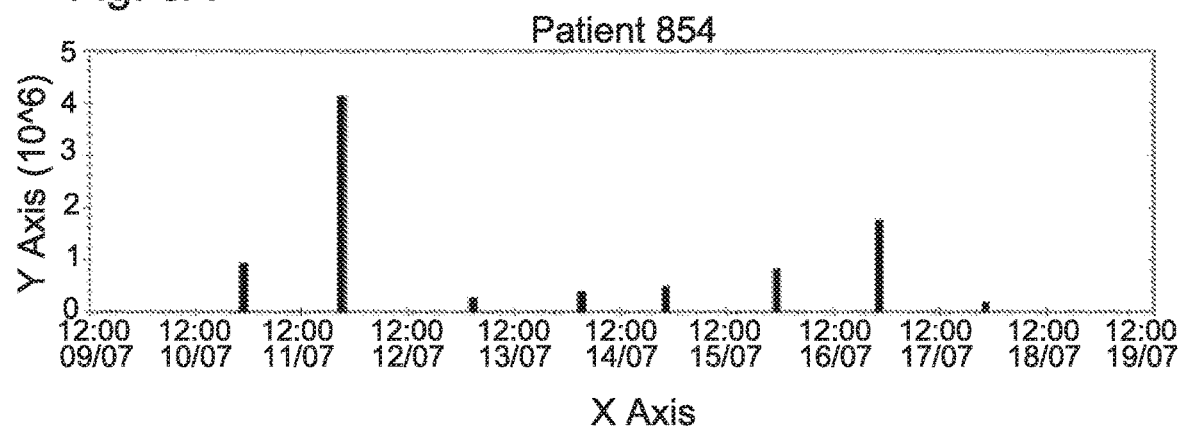
FIGS. 8A-8C provide bacterial load *S.Aureus,Act, Acineto-bacter* and *Pseudo-monas*, respectively of a patient.
Figure 8B:
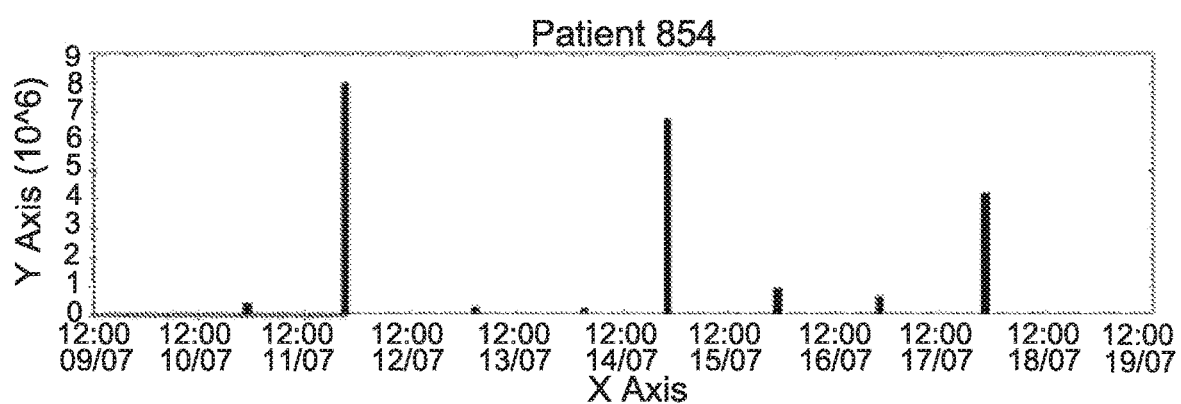
Figure 8C:
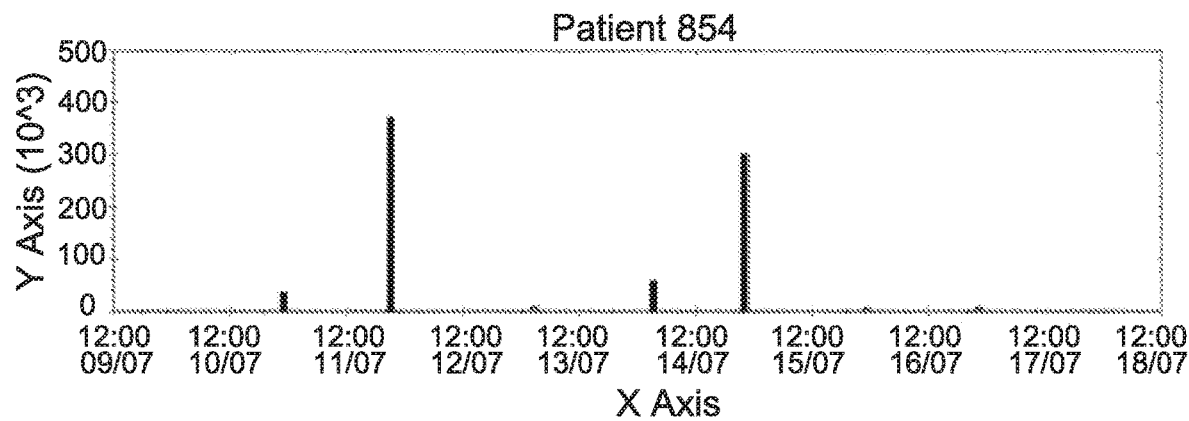

In FIGS. 8A, 8B and 8C, the bacterial load of three known bacteria in a certain patient diagnosed according to the present invention are displayed. In particular, *S. Aureus, Act, Acineto-bacter* and *Pseudo-monas*, respectively are demonstrated.

Figure 9C:
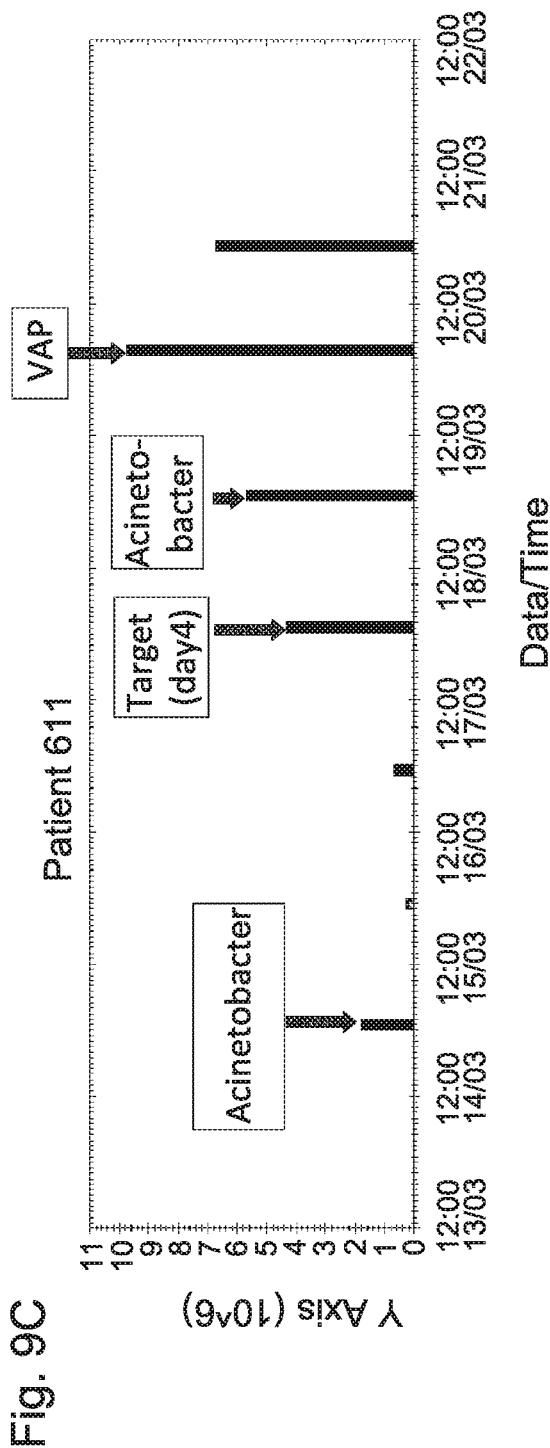
Figure 9D:
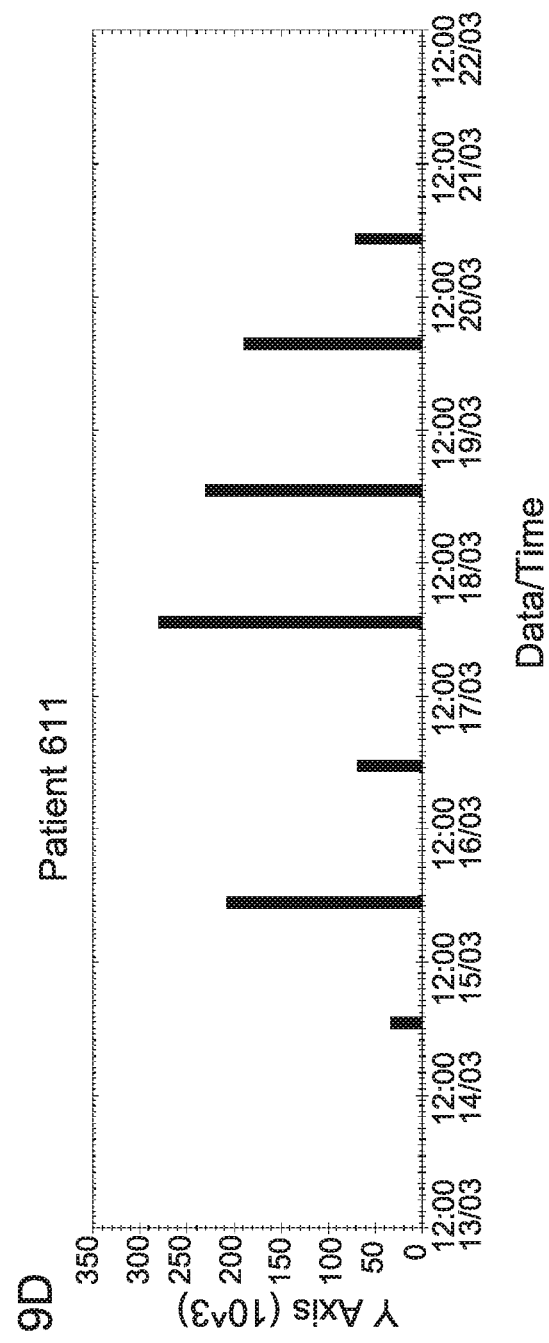
Figure 9E:
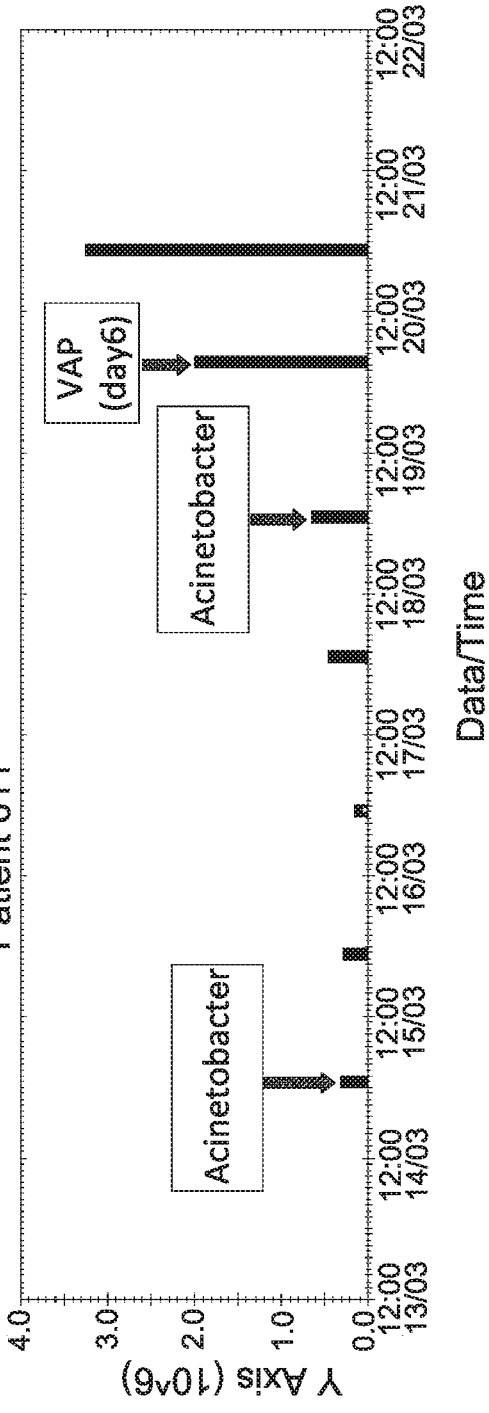

Turning to FIGS. 9A-9E, the detection of a bacterial load of *Acinetobacter* (FIG. 9B, FIG. 9C), *Pseudomonas* (FIG. 9D) and *klebsiella* (FIG. 9E) is demonstrated. The referral of "*Acinetobacter*" with a specific indication of a day, i.e. "day 1", "day 5", etc. relates to the findings of the bacterium by a conventional method of taking lavage from the lung, growing on an appropriate substrate, and detecting by time of flight. The reason for the conventional method of finding only *Acinetobacter* is associated with the mechanism with which it is carried, i.e. the exact location in the lung the lavage is taken, the development of the colonies on the growth medium and the sample taken for analysis. The results of the present invention are given as concentrations of peaks representing target molecules that vary in amount over time. Hence of the 2461 compounds that are detected by the GC-Ms system (FIG. 9A), only the concentrations of 41 target compounds (previously elucidated) are elected (FIG. 9B). FIG. 9C demonstrates the concentrations of 20 compounds characteristic of *Acinetobacter* (previously elucidated) and their development over time. Clearly the presence of growing amounts of *Acinetobacter* is already found on the $4^{th}$ day, prior to the detection of VAP by conventional means (X-ray). FIG. 9D demonstrates the same for *Pseudomonas* and FIG. 9E for *klebsiella*. Hence while the conventional route is restricted to the efficiency in the extraction of lavage (depth and location in the lung), the present invention samples all compounds exhaled and therefore provides a fuller more detailed picture of ALL bacterium that are present as each of these bacteria is reflected by its characteristic compounds—target compounds.

Figure 10A:
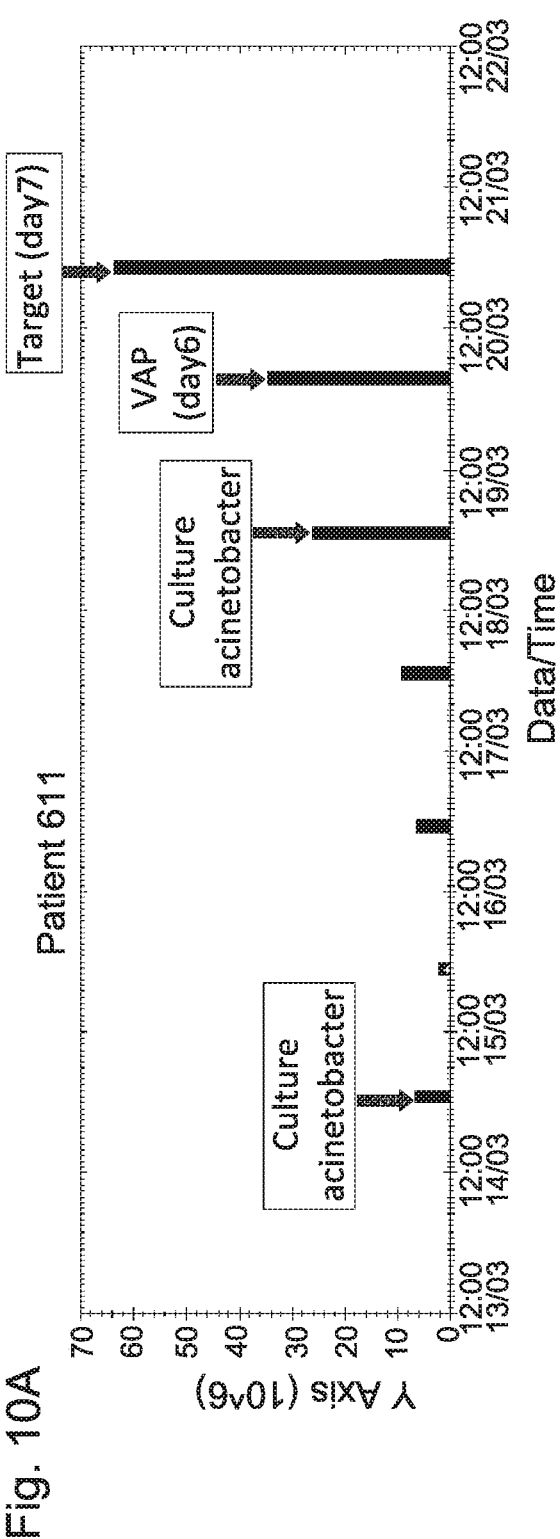
FIGS. 10A-10D provide detection of bacterial load by detecting functional groups that were previously found to be characteristic of a certain bacterium.
Figure 10B:
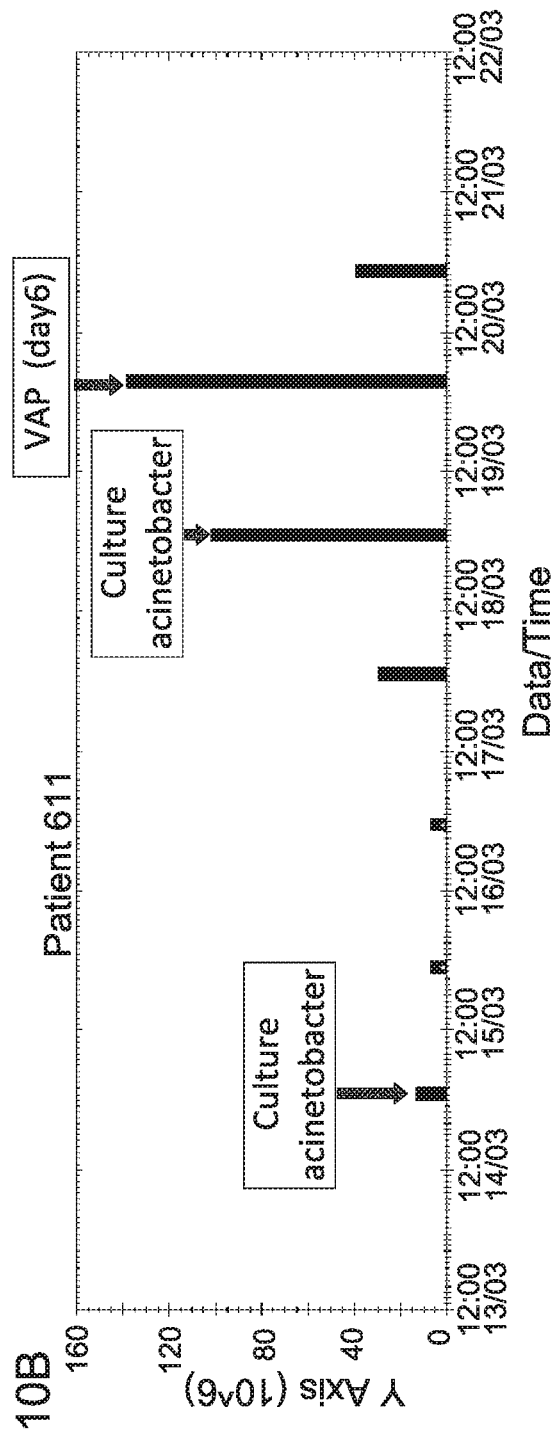
Figure 10C:
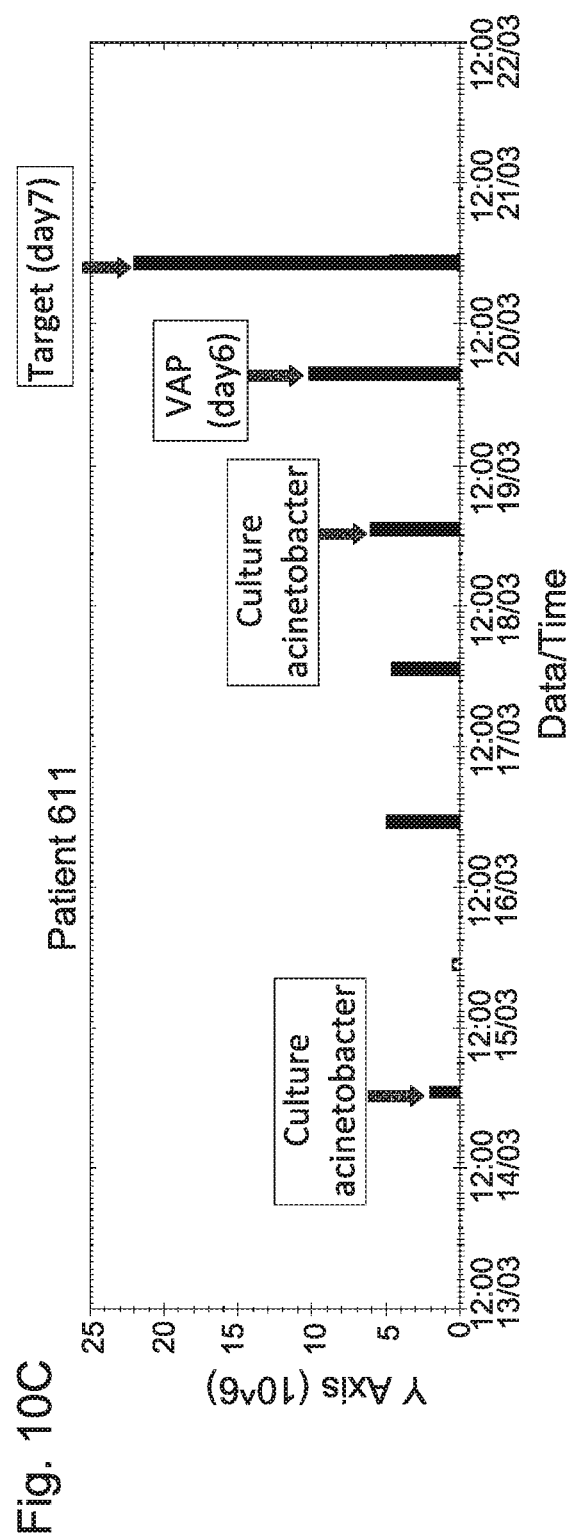
Figure 10D:
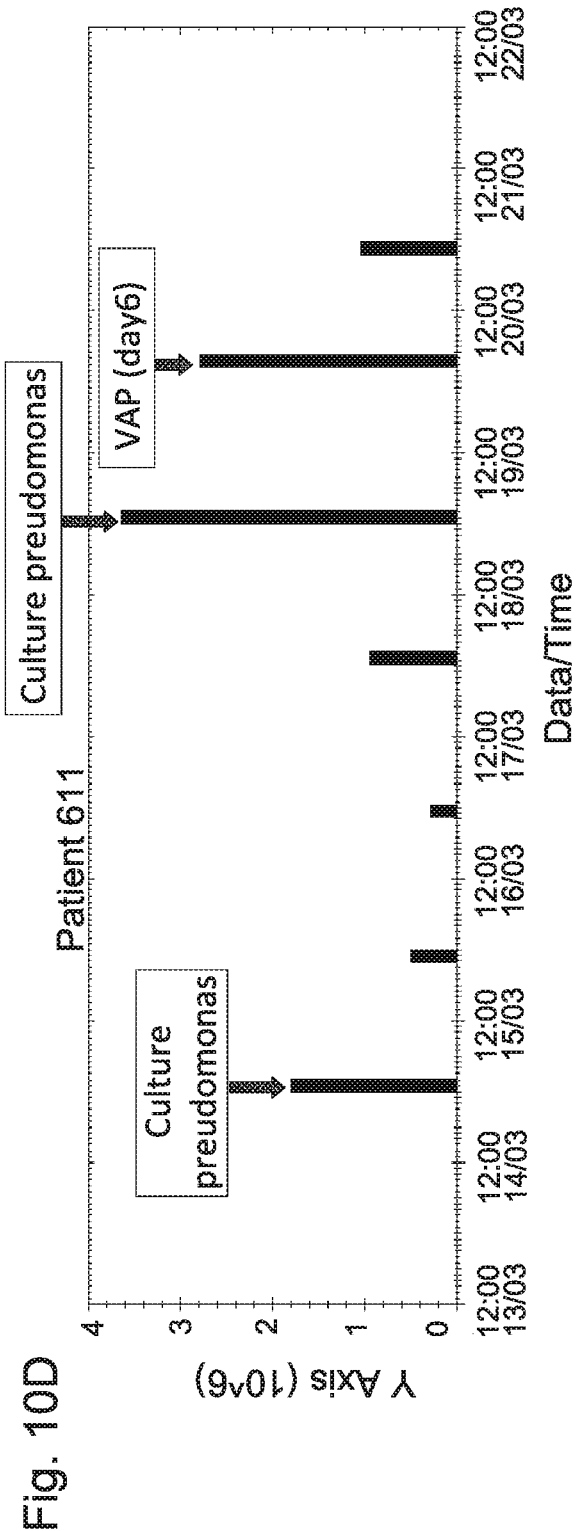

Turning to FIGS. 10A-10D, the detection of the bacterial load of *Acinetobacter* (FIG. 10C) and *Pseudomonas* (FIG. 10D) is demonstrated. The referral to "*Acinetobacter*" or "*pseudomonas*" with a specific indication of a day, i.e. "day 1", "day 5", etc. relates to the findings of the bacterium by a conventional method of taking lavage for the lung, growing on an appropriate substrate, and detecting by time of flight. The results according to the method of the present invention are given as concentrations of peaks representing molecules that vary in amount over time. FIG. 10A demonstrates detection of alcohols (277 compounds) that are characteristic of bacteria (previously elucidated). FIG. 10B demonstrates detection of aldehydes (789 compounds) that are characteristic of bacteria (previously elucidated). FIG. 10C provides the detection of *Acinetobacter* based on its (previously elucidated) 19 compounds and FIG. 10D provides the detection of *Pseudomonas* based on its (previously elucidated) 16 compounds.

Figure 11A:
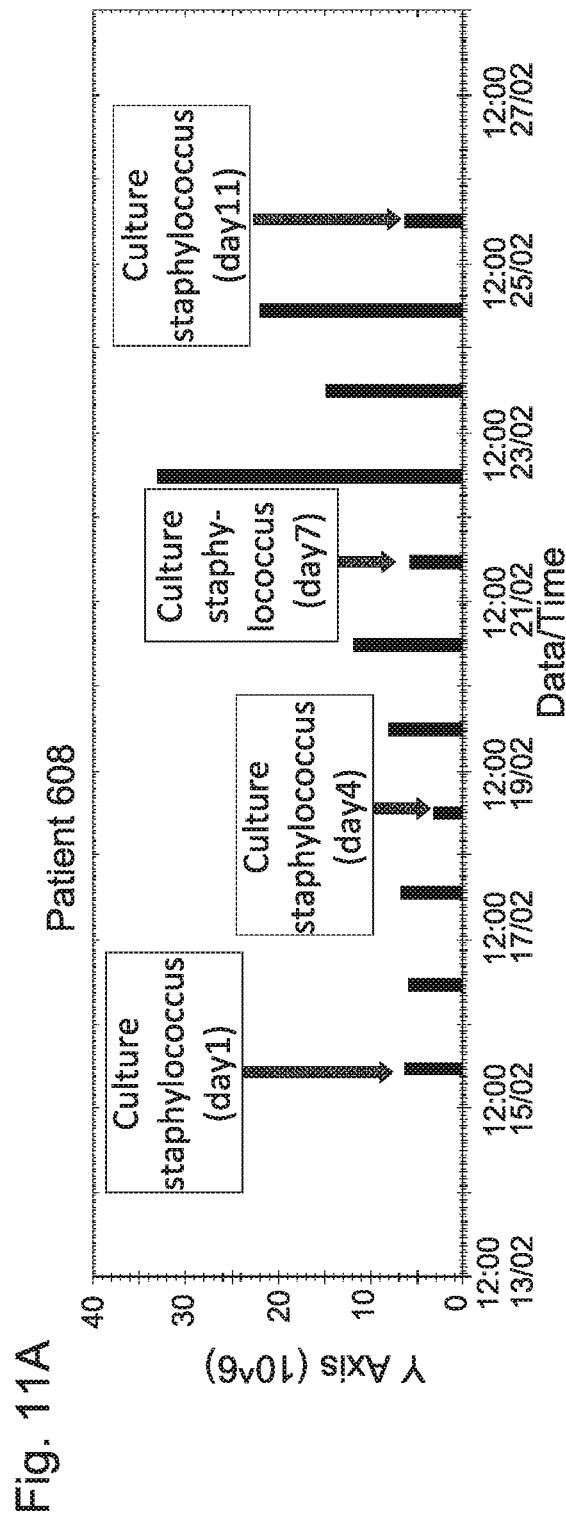
Figure 11D:
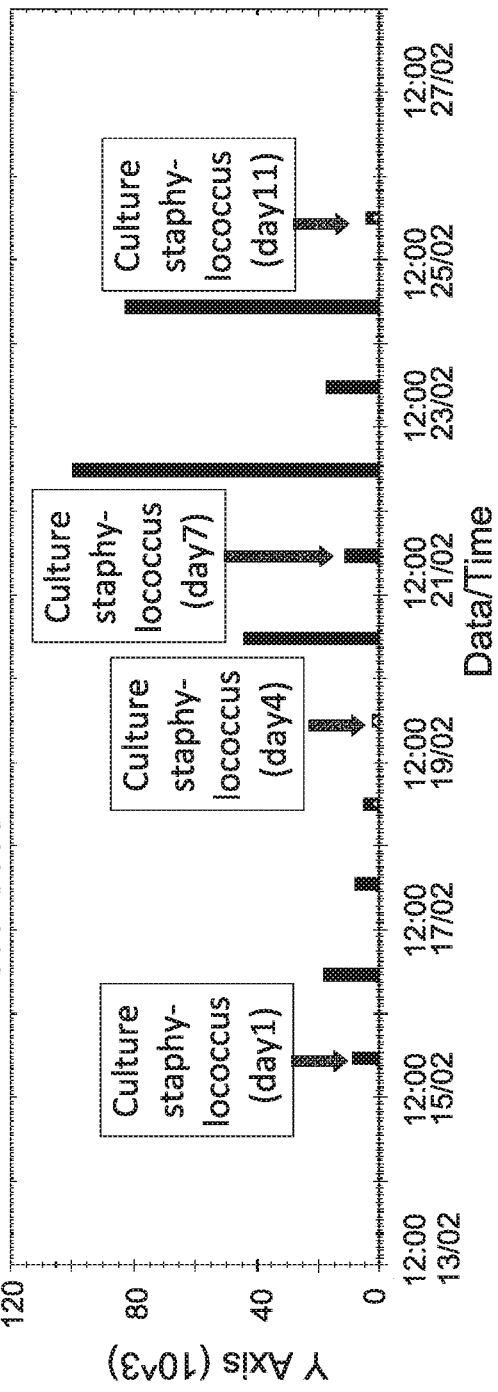

Turning to FIGS. 11A-11D, the detection of bacterial load of three different bacteria based on specific compounds (previously elucidated) is demonstrated. The referral to "Culture *Staphylococcus*" with a specific indication of a day, i.e. "day 1", "day 5", etc. relates to the findings of the bacterium by conventional method of taking lavage for the lung, growing on an appropriate substrate, and detecting by time of flight. Hence FIG. 11A provides the concentrations of 40 target compounds that have previously been elucidated as belonging to these bacteria. FIG. 11B shows the detection of 1-ethyl,4-methyl-benzene indicative of the presence of *Staphylococcus*. FIG. 11C shows the detection of 1,3-dimethyl-benzene indicative of the presence of *Pseudomonas Aeruginosa* and FIG. 11D shows the detection of benzaldehyde indicative of the presence of *Klebsiella*.

Figure 12A:
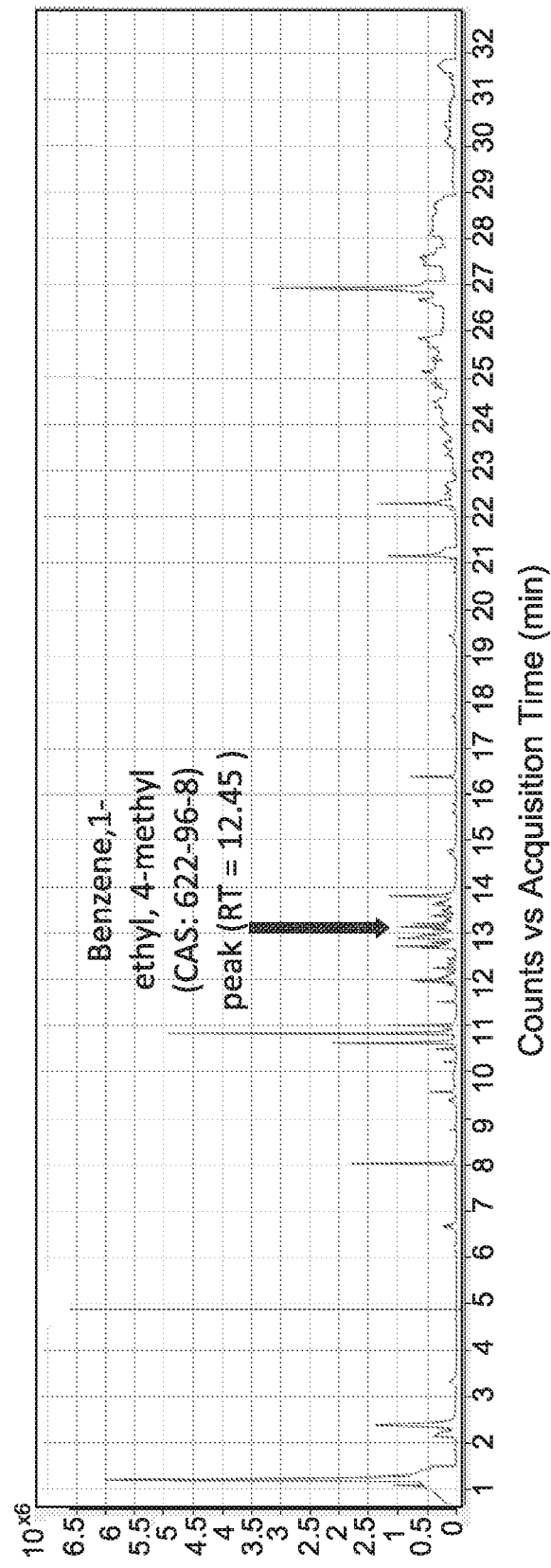
Figure 13A:
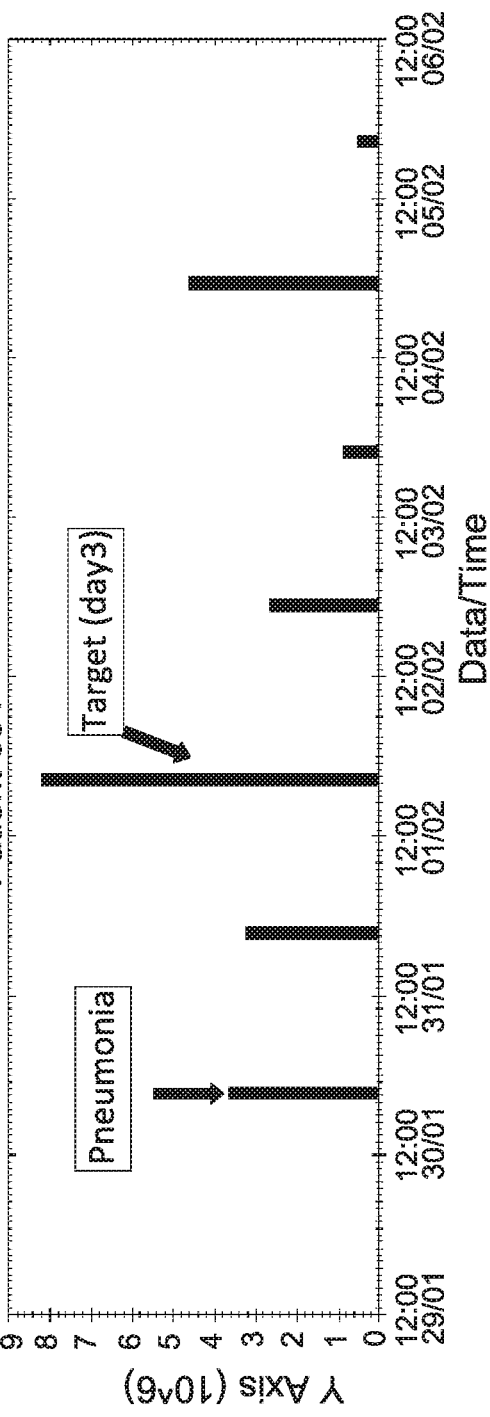
FIGS. 13A-13F provide concentrations of compounds indicative of 3 specific bacteria in patients diagnosed with pneumonia vs. healthy individuals.
Figure 13B:
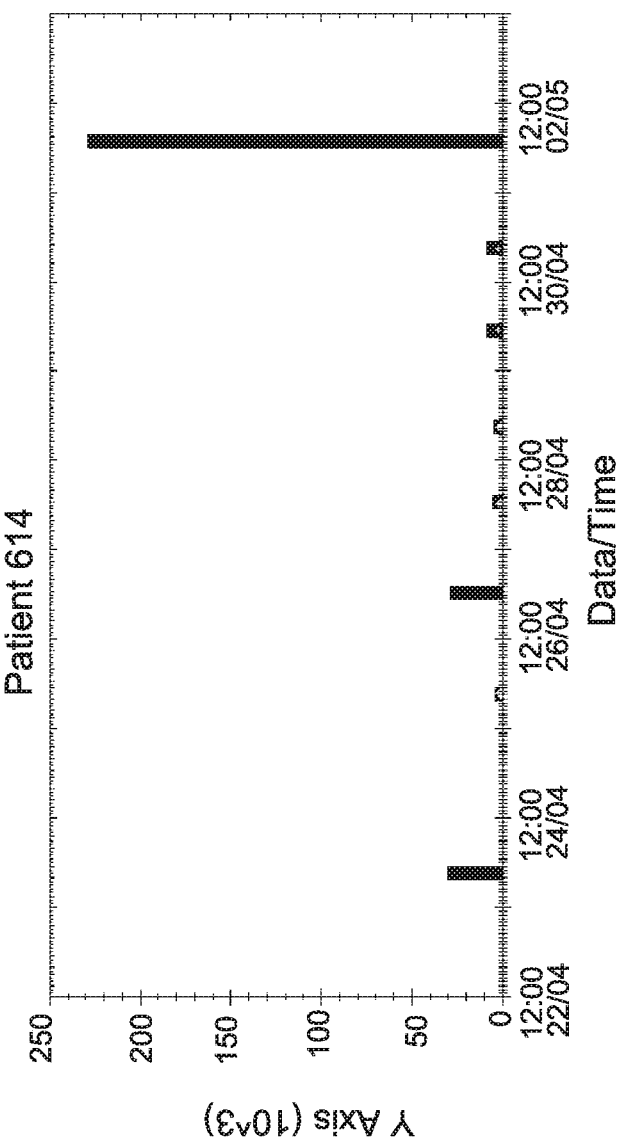
Figure 13C:
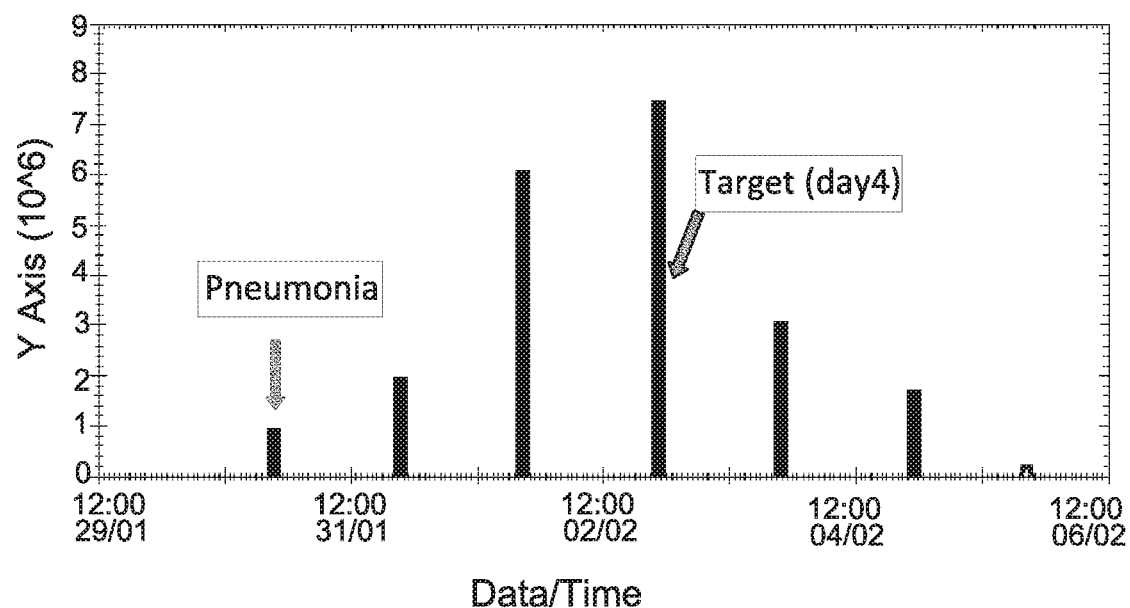
Figure 13D:
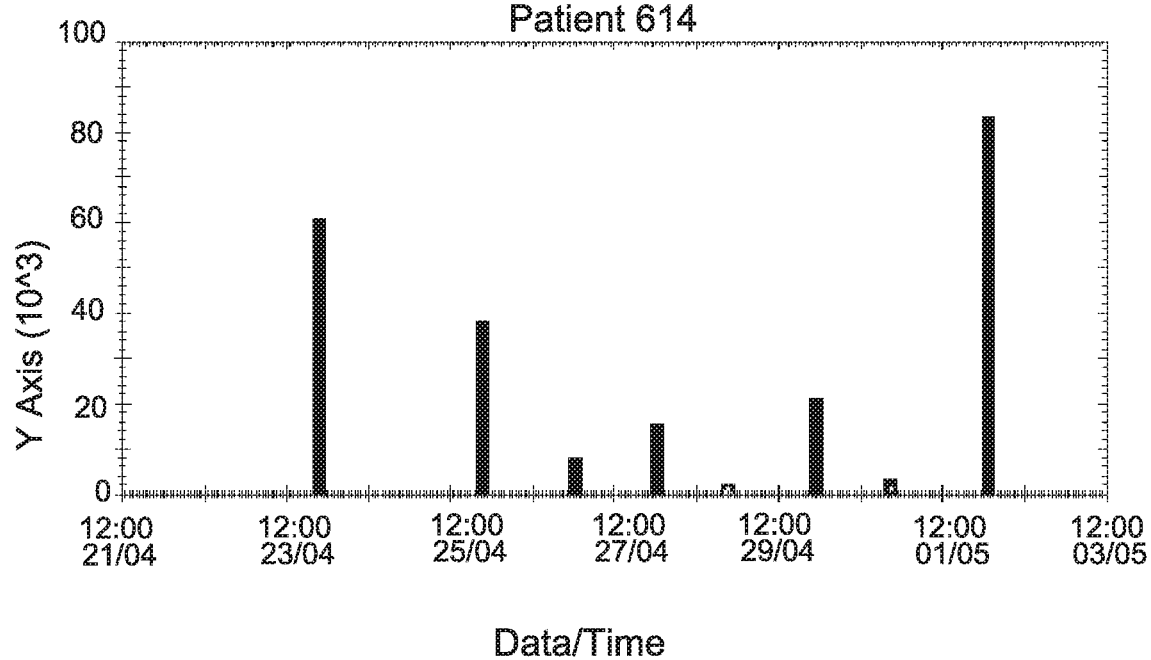
Figure 13E:
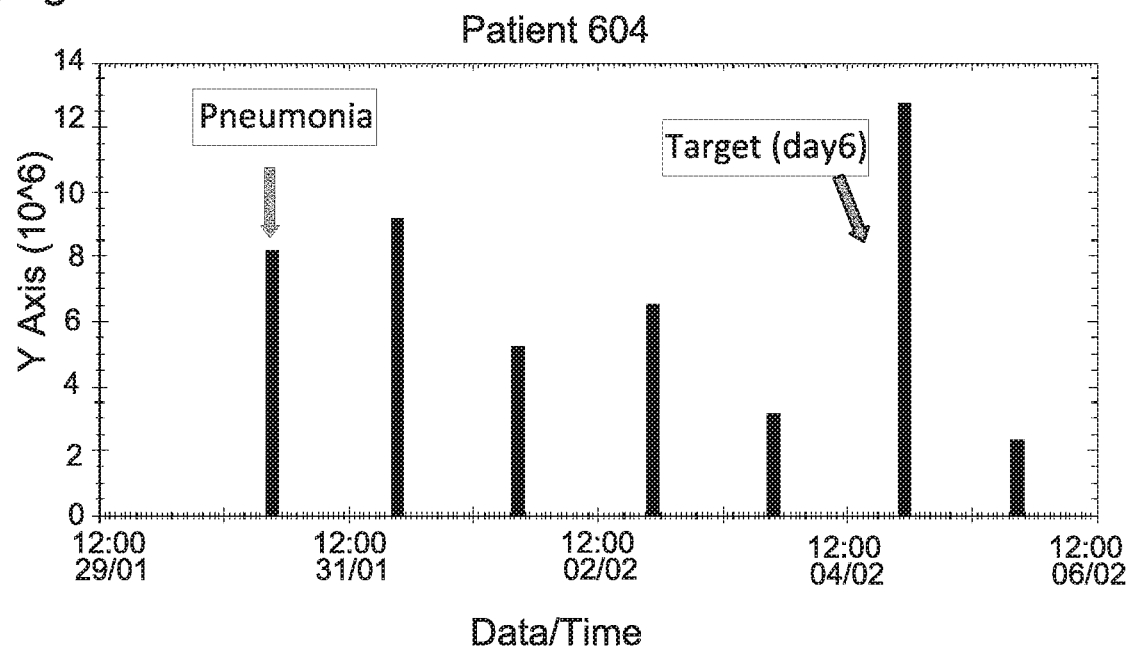
Figure 13F:
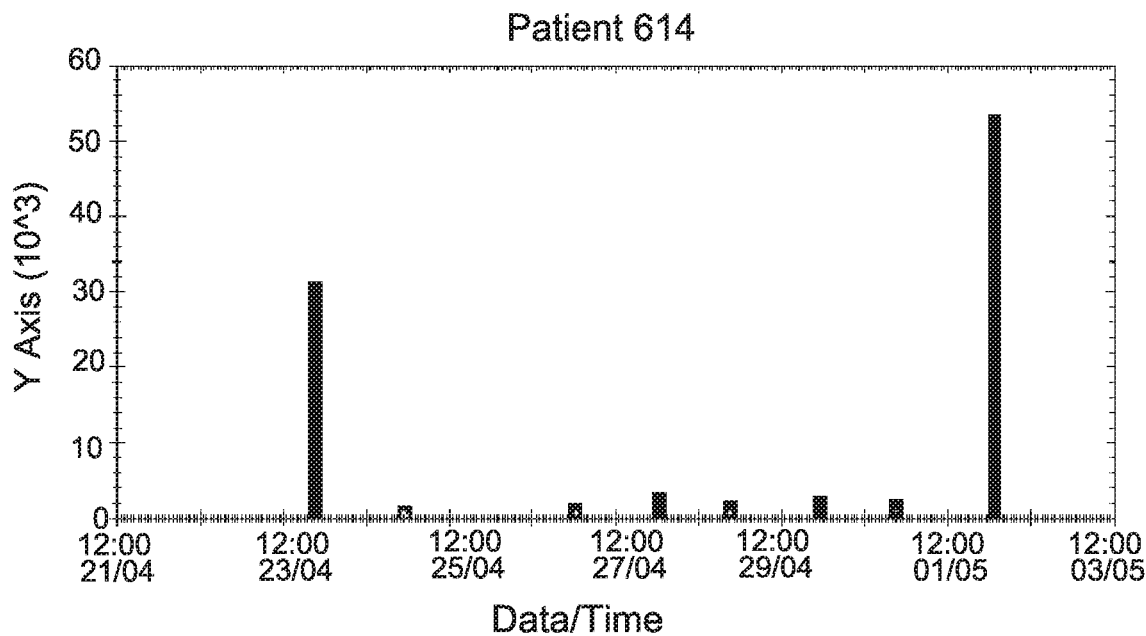

In FIGS. 12A-12D the method for determining the amount of each of the compounds according to the invention is given. FIG. 12A shows part of the chromatogram including numerous compounds among them 1-ethyl, 4-methyl-benzene (FIG. 12E) identified according to its retention time. It is however buried under many other compounds. FIG. 12B demonstrates the deconvolution that is done in order to detect more specifically the peak of this specific compound. FIG. 12C is yet a further enlarged demonstration of the result of the deconvolution. FIG. 12D shows the isolated peak of this specific compound that enables to calculate its area (area under the curve) thus determining its concentration in the exhaled air.

Turning to FIGS. 13A-13F, concentration of three typical bacterium associated with pneumonia are given. Patients diagnosed with pneumonia have a concentration of compounds that are indicative of the specific bacterium in the scale of $0.2\text{-}20 \times 10^6$ whereas health individuals have a concentration of compounds that are indicative of the specific bacterium in the scale of $0.2\text{-}200 \times 10^3$. Thus, FIGS. 13A, 13C and 13E demonstrate patients diagnosed with pneumonia while FIGS. 13B, 13D and 13F demonstrate healthy individuals.

EXPERIMENTAL

The sampling or collecting units that were used contained sorbents selected from TENAX™, i.e. Poly (2,6-diphenyl-p-phenylene oxide) (PPPO), CARBOXEN®, i.e. Sulfonated polymers; Carbon molecular sieves that are prepared by the controlled pyrolysis of poly (vinylidene chloride) or sulfonated polymers. Carbon adsorbents used according to the invention include CARBOTRAP® F, CARBOTRAP® C, CARBOTRAP® Y, CARBOTRAP® B, CARBOTRAP® X, CARBOPACK™ F, CARBOPACK™ C, CARBOPACK™ Y, CARBOPACK™ B, CARBOPACK™ X, CARBOXEN® 1016, CARBOXEN® 569, CARBOXEN® 1021, CARBOXEN® 1018, CARBOSIEVE™ S-III, CARBOXEN® 1003, CARBOSIEVE™ G, CARBOXEN® 1000 and CARBOXEN® 1012.

Carbon adsorbents may also be selected amongst graphitized carbon blacks having a 20/40 mesh, graphitized carbon blacks having a 60/80 mesh and carbon molecular sieves. In some embodiments, the adsorbents having a surface area between 5 and 1500 m2/g, a density of between 0.2 and 0.7 and/or a micropore diameter between 4 and 300 A.

Thermal desorption units for desorbing volatiles adsorbed to the sampling units were selected from Markes TD100-xr (Autosampler), TD-100 cold traps, including Stainless steel thermal desorption sorbent tubes. Perkin Elmer Turbo Matrix 650 ATD Thermal Desorption System, including Stainless steel thermal desorption sorbent tubes. Shimadzu TD-20 or TD-30 Thermal Desorption System, including Stainless steel thermal desorption sorbent tubes. Gerstel TDS 3C/TDS-A2 Thermal Desorption System, including Stainless steel thermal desorption sorbent tubes. Scientific Instrument Services (SIS) TD-5 Thermal Desorption System, including Stainless steel thermal desorption sorbent tubes. CDS 9300 Thermal Desorption System with CDS 7550 Autosampler, including Stainless steel thermal desorption sorbent tubes. CDS 7550S Stand-gone 72 position Thermal Desorption system, including Stainless steel thermal desorption sorbent tubes.

The analytical system, GC, MS and GCMS were selected form GCMS with TOF, Marke BenchTOF-HD, Time-of-flight mass spectrometer for GC ALIGENT® 7890 and GC×GC modulator, including the option of collecting different collision energies at the same time. Quadrupole GCMS, ALIGENT® GC 7890B with ALIGENT® MSD 5977B, ALIGENT® GC 6890 with ALIGENT® MSD 5975, Quadrupole GCMS, ALIGENT® GC 7890 with ALIGENT® MSD 5975, Quadrupole GCMS, ALIGENT® GC 6890 with ALIGENT® MSD 5973, GCMS, ALIGENT® 7250 GC/Q-TOF, GCMS, ALIGENT® 7010B Triple Quadrupole GC/MS, GCMS, Thermo Scientific Q Exactive™ M GC Orbitrap™ M GC-MS/MS.

GC Column Samples: the GC separate the analytes using 2 capillaries columns. The first main non-Polar column) column was selected from the following: SGEPN 99054140 (SN: 073438A23), 20M×0.18 mmID-BPX5×0.18 µm df, with He flow of 0.5 ml/min (Constant flow/pressure), and the 2ed column is polar column. GC capillary column: ALIGENT® DB5-ms 30M×0.25 mmID×0.50 µm df, with He flow of 1.5 ml/min (Constant flow/pressure). GC capillary column: Zebron ZB-5, 30M×0.25 mmID×0.25 µm df, with He flow of 1.2 ml/min (Constant flow/pressure). GC capillary column: ALIGENT® DB5-ms 60M×0.25 mmID× 1.0 µm df, with He flow of 1.5 ml/min (Constant flow/pressure). GC capillary column: ALIGENT® DB5-ms 60M×0.53 mmID×1.4 µm df, with He flow of 5 ml/min (Constant flow/pressure). GC capillary column: ALIGENT® DB1 60M×0.32 mmID×0.5 µm df, with He flow of 2 ml/min (Constant flow/pressure). GC capillary column: ALIGENT® DB1 30M×0.18 mmID×0.25 µm df, with He flow of 0.6 ml/min (Constant flow/pressure). GC capillary column: ALIGENT® DB1 30M ×0.15 mmID×0.15 µm df, with He flow of 0.3 ml/min (Constant flow/pressure).

Calculation of Area Peak for Determining Growth of Bacterial/Viral/Fungal Mass

Compounds desorbed from the sampling units are analyzed using a GCMS instrument, after chromatographic separation in a capillary GC column. In the resulting MS chromatogram, all separated substances appear as chromatographic peaks, arranged by their retention times. Each peak consists of a continuous line connecting several points, wherein each point is the sum of abundances of fragment ion generated from the fragmentation of the material molecules. The peak area is calculated by performing an integral derivative of the abundance of ions according to the time ($d_{abundance}$/dt) from the starting point of the peak to its end, as derived from Eq. 1:

$$\int_{PS-T}^{PE-T} \frac{da}{dt} = \text{peak area.} \quad \text{(Eq. 1)}$$

wherein in Eq. 1, PS-T is the peak start time, PE-T is the peak end time, da is the derivative of the ion's abundance, and dt is the derivative of the retention time.

It should be noted that peak area values vary between GCMS instruments, as well as by integration software used. However, since a disease onset or a bacterial/viral/fungal load is determined by a determining a change between two consecutive measurements, for each subject, by using the same GCMS instrument, the determination is indicative and conclusive.

In order to calibrate the peak area of each marker, a known substance is used as an internal standard (IS) and is inserted into the sampling unit. The IS is used in a known concentration, volume and pressure (e.g. volume of 1 ml standard gas with 3 ppm of the IS compound, at an inlet pressure of 25 psi). The peak areas are normalized according to the IS area utilizing a known and accepted IS calculation method. Three non-limiting examples of IS used in accordance with the invention are shown in Table 1.

marker peaks, throughout the days of hospitalization. These give an index regarding the changing/developing in the bacterial load (BL), viral load (VL) or fungal load (FL) in the patient's respiratory system, i.e. in the lungs. An increase in the peak area of about 50% or more is considered a significant change that reflects an increase in bacterial load. In the case of an increase of about 50% in the marker peaks area, the algorithmic way in which the development of an infectious disease is described is follows:

If the total biomarkers compounds (TBCM) area of the $2^{nd}$ day is greater (over 50%) compared to the patient's baseline ($1^{st}$ day), and the TBCM area of the $3^{rd}$ day is greater (over 50%) than the TBCM area of the $2^{nd}$ day, this servers an indication of a significant increase in bacterial/viral/fungal load (BL/VL/FL), which should be reported and continued to be monitored.

Assessing the Development of Infectious Disease Such as VAP

The algorithm that shows signs of growth in the bacterial or viral load makes it possible to give an assessment regarding the bacterial family or the type of virus or fungi. The algorithm contains various metrics that consider the peak area size of the biomarkers, the biomarkers numbers, the type of biomarkers and the ratio between them. Hence the algorithm includes, inter alia, data concerning bacterial/viral/fungal load, markers, total marker compounds, general markers, bacterial/viral/fungal number and others.

The Following examples are based on 36 patients that were enrolled in the trials. 28 patients were included in actual trials (that required sampling for at least 3 days). Of the 28 patients, 6 patients were recognized as potential VAP cases (z20%) by using the analysis of exhaled breath samples of ventilated patients according to the invention.

TABLE 1

3 Internal Standard molecules used for VAP detection.

| IS # | Compound Name | CAS RN | Formula | Average RT | Conc.-ppm (v/v) | Average Area | Relative Standard Deviation (%) |
|---|---|---|---|---|---|---|---|
| S-1 | Methane, bromochloro- (IS1) | 74-97-5 | $CH_2BrCl$ | 10.22 | 3.0 | 466,103 | 30 |
| S-3 | Chlorobenzene-d5 (IS3) | 3114-55-4 | $C_6ClD_5$ | 17.64 | 3.0 | 2,120,000 | 30 |
| S-4 | p-Bromofluorobenzene (IS4) | 460-00-4 | $C_6H_4BrF$ | 20.39 | 3.0 | 2,779,000 | 30 |

A marker area size of 1,000 ($10^3$) calculated by Eq. (1) above is approximately equivalent to a concentration of 0.006 ppm (v/v) of IS-1. An area of 1,000,000 ($10^6$) is approximately equivalent to a concentration of 6.4 ppm (v/v) of IS-1.

Assessment of the Development of a Disease Based on a Calculated Area

Each patient arriving/brought for prolonged hospitalization caries their own medical background, thus by analyzing the patient's exhaled air upon arrival according to the present invention, a baseline that characterizes the specific patient is created (Patient Baseline). The patient's baseline or marker background level is calculated by the sum of all areas measured for the marker peaks, that appear in his exhaled breath.

An assessment of the development of an infectious disease is carried out while monitoring the total areas of the Target Molecules (TMs) indicating specific bacterial mass growth that are attributed to bacteria associated with VAP were detected in all 6 patients. Important to note is that as exemplified below the TMs were detected in exhaled air of the patients one, two and three day prior to finding of the standard-of-care clinical signs of VAP. These standard-of-care clinical signs include a new and persistent (>48-h) or progressive radiographic infiltrate plus two of the following: temperature of >38° C. or <36° C., blood leukocyte count of >10,000 cells/ml or <5,000 cells/ml, purulent tracheal secretions, gas exchange degradation and significant bacterial growth of a tracheal secretion sample. All 6 patients were thus isolated as potential VAP cases, where their VAP was later confirmed the treating physicians/medical staff of the ICU through monitoring of patient's clinical signs and symptoms over the course of his ICU stay.

Example 1

A 56-year old male, generally healthy, presented with acute flu (viral upper respiratory infection) was admitted to ICU in Sheba hospital (Ramat Gan, IL) for mechanical ventilation support. The patient remained under ventilation for 9 days and was released from hospital on day 12. The clinical parameters are given in Table 2:

TABLE 2

| Patient | Day 2 | Day 3 | Day 4 | Day 5 | Day 6 | VAP | Day 8 | Day 9 |
|---|---|---|---|---|---|---|---|---|
| Temperature | 36.8 | 37 | 36.2 | 36.3 | 36.6 | 36.3 | 36.3 | 37.3 |
| WBC (white blood cell) | 2.6 | 3.22 | 4.96 | 4.05 | 3.58 | 3.06 | 3.68 | 4.51 |
| CRP (C reactive protein) | 131.86 | 71.38 | 43.76 | 120.6 | 259.12 | 203.49 | 134.33 | 88.54 |
| Antipyretic | n | n | n | N | n | n | N | n |
| Culture | negative | nd | nd | nd | Pseudomon | nd | Nd | nd |
| Antibiotics | Tazocin | same | same | same | same | Ciprofloaxcin | Same | same |
| X-Ray | 2 | 1 | 1 | 1 | 1 | 4 | 4 | 3 |
| Biomarkers | 3 | 2 | 2 | 5 | 4 | 4 | 3 | 3 | n = negative; y = yes; nd = not done; X-ray and biomarkers = numbers 1-5 indicate level where 1 = normal and 5 = very high Analysis of the patient's exhaled air detected markers. In particular, 4 specific *pseudomonas*-specific markers were detected already on day 1 prior to the detection of clinical signs. Hence the analysis of the exhaled air detected biomarkers two days prior to the X-Ray and 2-3 days prior to the detection by culture. Therefore, VAP was detected much earlier than clinical signs that are routinely used.

All biomarkers spiked on day 5. The spiking of the marker designated No. 4 was significantly more than the others. This is associated with exponential growth. Thus, VAP occurred in the patient while under antibiotic therapy. As a consequence of its detection, the antibiotic treatment was revised following clinical signs of VAP.

Example 2

A 24-year old male, admitted to neurosurgical ICU in Rambam hospital (Haifa, IL) following severe fall from height, suffering from scull base fracture, epidural hemorrhage, lung contusion and traumatic pneumothorax. The man was placed on mechanical ventilation support for 13 days. The patient died on day 15. The clinical parameters are given in Table 3:

TABLE 3

| Day | 1 | 2 | 3 | 4 | 5 | 6 | 7 VAP |
|---|---|---|---|---|---|---|---|
| Temperature | 36.4 | 36.5 | 37.4 | 37.8 | 37.9 | 338.8 | 337.4 |
| WBC (white blood cell) | 18.9 | 11.88 | 10.56 | 11.26 | 15.49 | 118.3 | 117.02 |
| CRP (C reactive protein) | | | | | | 42.41 | |
| Culture | | | | | | Gram (+) bacillus, B. cereus | Gram (+) bacillus, S. aureus |
| Antibiotics | Cefamezin | Csame | na | na | na | Tazocin | Tazocin |
| X-Ray | | | 33 | 3 | 33 | 33 | |
| Staph (MRSA) | 2 | | 22 | 00 | 66 | 22 | 00 |
| Acinetobacter | 0 | 00 | 13 | 00 | 22 | 33 | 00 |
| Klebsiella | 0 | 00 | 11 | 00 | 88 | 00 | 00 |

TABLE 3-continued

| Day | 8 | 9 | 10 | 11 | 12 | 13 |
|---|---|---|---|---|---|---|
| Temperature | 36.3 | 37.7 | 37.1 | 38.4 | 36.4 | 36.2 |
| WBC (white blood cell) | 16.88 | 12.23 | 14.64 | 12.91 | 12.58 | 99.31 |
| CRP (C reactive protein | | | 87.36 | | 31.97 | |
| Culture | | | | | | |
| Antibiotics | Tazocin, Vanco. | Tazocin, Vanco. | Tazocin, Vanco. | Tazocin, Vanco. | Tazocin, Vanco. | Tazocin, Vanco. |
| X-Ray | 85 | 33 | | | | |
| Staph (MRSA) | 00 | 00 | 22 | 22 | | 00 |
| Acinetobacter | 22 | 00 | 00 | 22 | | 00 |
| Klebsiella | 00 | 00 | 22 | 22 | 00 | 00 | n = negative; y = yes; nd = not done; X-ray and biomarkers = numbers 1-5 indicate level where 1 = normal and 5 = very high Analysis of the exhaled air detected biomarkers. In particular, 3 different bacteria were detected with different concentrations and different daily appearances. Culture detected only 1 bacterial source (MRSA). The total bacterial mass that was detected spiked on day 5, being 2 days prior to the clinical diagnosis that pointed to VAP and 2 to 3 days before the culture (that itself requires 1 or 2 days for analysis).

Example 3

A 34-year old male, admitted to neurosurgical ICU at Rambam hospital (Haifa, IL) for head trauma following severe fall, suffered from traumatic scull base fracture, subdural and epidural hemorrhage, multiple ribs fractures, lung contusion and pneumothorax. He was placed on mechanical ventilation support for 7 days. Released from hospital on day 14. The clinical parameters are given in Table 4:

It should further be noted that bacterial mass detected two spikes ($2^{nd}$ and $5^{th}$ days) where the data of the $2^{nd}$ day is unique.

Example 4

Markers identified for Staphy Aureus were bromochloro methane, 1,4-difluoro benzene, chlorobenzene, p-bromo-fluorobenzene, 3-methylbutanal, 2-methylbutanal and dimethyl trisulfide.

The invention claimed is:
1. A method for identifying in a breath sample from a subject an early onset of a bacterial disease state and treating the bacterial disease state by detecting the presence of at least one disease-associated cluster of volatile compounds indicative of the bacterial disease, the method comprising;
at a first time, exposing a first breath sample of the subject to at least one first sampling unit comprising one or

TABLE 4

| Day | 1 | 2 | 3 | 4 | VAP | 6 | 7 | 8 |
|---|---|---|---|---|---|---|---|---|
| WBC | 7.4 | 7.68 | 7.4 | 12.38 | 12.67 | 11.54 | 11.22 | 10.59 |
| CRP | Na | Na | Na | Na | Na | na | Na | na |
| Antipyretic | Na | Na | Na | Na | Na | na | Na | na |
| Culture | | | | | Lower respire. tract cult. results | | | |
| Antibiotics | Rcephin Cefamezin | Rcephin Cefamezin | Rcephin Cefamezin | Rcephin Cefamezin | Rcephin, Cefamezin, Tazocin | Cefamezin, Tazocin | Cefamezin, Tazocin | cefamezin |
| X-Ray | 0 | 0 | 0 | 2 | 3 | 0 | 4 | 5 |
| S. Aureus $6 \times 10^6$ | 2 | 5 | 0 | 0 | 1 | 2 | 3 | 3 |
| Acinetobacter $12 \times 10^6$ | 0 | 4 | 0 | 0 | 4 | 2 | 2 | 3 |
| Pseudomonas $5 \times 10^3$ | 1 | 4 | 1 | 1 | 3 | 0 | 0 | 0 | n = negative; y = yes; nd = not done; X-ray and biomarkers = numbers 1-5 indicate level where 1 = normal and 5 = very high Analysis of the exhaled air detected biomarkers. In particular, 3 different biomarkers, i.e. three different bacteria with different concentrations and different daily appearances were detected. Contrary to these findings, culture detected only 1 bacterial source. The total bacterial mass that was detected spiked on the $5^{th}$ day. These findings were revealed 2 days before X-Ray diagnosis and 1 or 2 days before culture (1, 2 days required for analysis of culture).

more adsorbing regions capable of reversibly associating volatile compounds in said breath sample, the adsorbing region being different from a metallic surface or metallic nanoparticle, desorbing adsorbed compounds, analyzing an identity of the adsorbed compounds after desorbing the adsorbed compounds, and determining a level of the at least one disease-associated cluster of volatile compounds;

at an at least one consequent further time point, exposing a breath sample of the subject to a further sampling unit comprising one or more adsorbing regions capable of reversibly associating to volatile compounds in said breath sample, desorbing a adsorbed compounds, analyzing an identity of the adsorbed compounds after desorbing the adsorbed compounds, and determining a level of the at least one disease-associated cluster of volatile compounds;

comparing the level of the cluster of volatile compounds associated with said disease of said at least one first sampling unit and the level of said further sampling unit;

wherein an increase or a decrease of at least 50% in the level associated with the further sampling unit compared to that of the first sample unit is indicative of the early onset of said disease state; and responsive to comparing the level of the cluster of volatile compounds, beginning a therapeutic treatment or modifying the therapeutic treatment.

2. The method according to claim 1, wherein each of the one or more adsorbing regions is configured to reversibly associate to the volatile compounds in said breath sample.

3. The method according to claim 1, wherein the one or more adsorbing regions being formed of a solid adsorbent configured to physically trap the volatile compounds, selected from the group consisting of at least one material selected from organic porous polymers, ion-exchange resins, carbon molecular sieves, and sulfonated polymers, a material selected amongst carbon adsorbents, carbon allotropes or carbonaceous materials, wherein the one or more adsorbing regions is a material having a surface area between 5 and 1500 m$^2$/g, a density of between 0.2 and 0.7 and/or a micropore diameter between 4 and 300 A.

4. The method according to claim 1, wherein following exposure of the one or more adsorbing regions to a breath sample, said adsorbing regions are treated to cause desorption or dissociation of the volatile compounds from the surface, and analyze the desorbed volatiles.

5. The method according to claim 4, wherein the volatile compounds are analyzed by gas-chromatography (GC), GC-lined mass-spectrometry (GC-MS), proton transfer reaction mass-spectrometry (PTR-MS), electronic nose device (E-nose), quartz crystal microbalance (QCM), infra-red spectroscopy (IR) or ultraviolet spectroscopy (UV).

6. The method according to claim 1, wherein the bacterial disease is caused by a bacterium selected from *Bacillus anthracis; Clostridium botulinum; Francisella tularensis; Yersinia pestis; Burkholderia pseudomallei; Burkholderia mallei; Clostridium perfringens; Coxiella burnetii; Brucella melitensis, abortus,* suis and *canis; Staphylococcus aureus; Rickettsia prowazekii; Chlamydia psittaci*; Food and Waterborne Pathogens such as *Escherichia coli, Vibrio cholerae, Salmonella* species, *Shigella* species, *Listeria monocytogenes, Campylobacter jejuni, Yersinia enterocolitica; Mycobacterium tuberculosis*; and other *Rickettsia*.

7. The method according to claim 1, wherein the disease is a hospital associated infection (HAI), caused by methicillin-resistant *Staphylococcus aureus* (MRSA), vancomycin-resistant enterococci (VRE), *Clostridium difficile, Acinetobacter baumannii*, or multi-drug resistant (MDR) *Acinetobacter* sp.

8. A method for determining an onset of ventilator-associated pneumonia (VAP) in a ventilated subject and treating the ventilated subject, the method comprising;
at a first time point, exposing a first breath sample from the ventilated subject to at least one first sampling unit comprising one or more adsorbing regions capable of reversibly associating to volatile compounds in said first breath sample, desorbing adsorbed compounds, analyzing an identity of the adsorbed compounds after desorbing the adsorbed compounds, and determining a level of at least one disease-associated cluster of volatile compounds;

at an at least one consequent further time point, exposing a breath sample from the ventilated subject to a further sampling unit comprising one or more adsorbing regions capable of reversibly associating to volatile compounds in said breath sample, desorbing adsorbed compounds, analyzing an identity of the adsorbed compounds after desorbing the adsorbed compounds, and determining the level of the at least one disease-associated cluster of volatile compounds;

comparing the level of the cluster of volatile compounds of a VAP-causing pathogen of said at least one first sampling unit and the level of said further sampling unit, wherein the VAP-causing pathogen is a bacterium;

wherein increase or a decrease of at least 50% in the level associated with the further sampling unit compared to that of the first sample unit is indicative of an early of onset of VAP; and responsive to comparing the level of the cluster of volatile compounds, beginning a therapeutic treatment or modifying the therapeutic treatment.

9. The method according to claim 8, wherein the at least one sampling unit is provided in a respiratory system used in ventilating the subject.

10. The method according to claim 8, wherein the at least one sampling unit is in a form of a vessel comprising the one or more adsorbing regions and allowing a timed residence contact of the breath sample with the one or more adsorbing regions.

11. The method according to claim 8, the method comprising detaching the at least one sampling unit from the outlet line of the respiratory system, desorbing the absorbed volatile compounds, and analyzing the volatile compounds to determine the level of volatile compounds adsorbed onto the one or more adsorbing regions.

12. The method according to claim 8, wherein analysis is carried out by a spectrometric method.

13. The method according to claim 1, wherein the bacterial disease is VAP.

14. The method according to claim 1 wherein the patient is a ventilated subject.

15. The method according to claim 8, wherein the at least one disease-associated cluster of volatile compounds includes compounds selected from those discharged to the surroundings by the disease-associated VAP pathogen, wherein the relative amounts of each of the volatile compounds produced and discharged to the surroundings of the pathogen are captured, identified and quantified forming a database of cluster of compounds indicative of the VAP pathogen.

16. The method according to claim 1, wherein the disease-associated cluster of volatile compounds comprises compounds selected from: 1,8-naphthyridine, 10-undecyn-1-ol, 3-methyl-1-butanol, 1-phenyl-1H-imidazole, 2-(2-pyridinyl)-1H-indole, 8-methyl-1H-purine, 1-methoxyphthalazine, 1-nitro-2-propanol, 2-butyl-1-octanol, 3,7-dimethyl-1-octanol, 2-methyl-1-propanol, 1-undecene, 2-(2-methylpropyl)-3,5-di (1-methylethyl)pyridine, 2,3-dimethylcyclohexylamine, 2,4-dithiapentane, 2-benzyl-1-methylpiperidine, 2-butanone, 3-propylidene-2-heptanone, 6-phenylhexanoic acid, 8-aminocaprylic acid, 2,2'-thiobisacetic acid, acetone, O-isopropyloxime benzaldehyde, 4-nitro-benzamide, 2-carboxy-benzeneacetic acid, 2-methyl-butanal, 3-methyl-butanal, 3-methyl-butanoic acid, dodecamethyl-cyclohexasiloxane, cyclohexene, D: C-Friedours-7-ene, dimethyl trisulfide, dimethyl disulfide, emorfazone (4-ethoxy-2-methyl-5-morpholin-4-ylpyridazin-3-one), ethylphenylhydantoin, gabapentin lactam, ethyl 5-oxohexanoate, 5-nitro-isoquinoline, lanostan-12-one, luminol (5-amino-2,3-dihydrophthalazine-1,4-dione), 4-butyl-phenol, phthalic anhydride, pregabalin, 1-(ethynylsulfinyl)-propane, ribo-ribo disaccharide, S-(2-benzothiazolyl) cysteine, and 2-butyl-5-ethyl-thiophene.

17. The method according to claim 1 wherein the further time point being from hours after said first time point to 1, 2, 3, 4, or 5 days after said first time point.

18. The method according to claim 8 wherein said further time point being from hours after said first time point to 1, 2, 3, 4, or 5 days after said first time point.

19. The method according to claim 18 wherein VAP is indicative after 48 hours.

20. The method according to claim 8, wherein the volatile compounds are selected from dimethyl disulfide, dimethyl trisulfide, 2-butanone, 2-methyl-butanal, 2,3-butanedione, butanoic acid-2-methyl-ethyl ester, 2-ethyl-1-hexanol, 3-methyl-butanal, and 2-methyl-1-propanol.

21. The method of claim 8, wherein the cluster of volatile compounds are selected from the group of dimethyl disulfide, dimethyl trisulfide, 2-butanone and 2-methyl-butanal; or from the group of dimethyl sulfide, 2,3-butanedione, butanoic acid-2-methyl-ethyl ester, and 2-ethyl-1-hexanol, 3-methyl-butanal.

22. The method according to claim 1, wherein the at least one disease-associated cluster of volatile compounds includes compounds selected from those discharged to the surroundings by the disease-associated pathogen, wherein the relative amounts of each of the volatile compounds produced and discharged to the surroundings of the pathogen are captured, identified and quantified forming a database of cluster of compounds indicative of the pathogen.

* * * * *